(12) United States Patent
Ayres et al.

(10) Patent No.: US 10,245,356 B2
(45) Date of Patent: Apr. 2, 2019

(54) MEDICAL DEVICES WITH NON-UNIFORM COATINGS FOR ENHANCED ECHOGENICITY

(71) Applicant: ENCAPSON B.V., Enschede (NL)

(72) Inventors: Lee Ayres, Enschede (NL); David Asrian, Enschede (NL); Johannes Antonius Opsteen, Enschede (NL); Dennis Manuel Vriezema, Enschede (NL)

(73) Assignee: ENCAPSON B.V., Enschede (NL)

( * ) Notice: Subject to any disclaimer, the term of this patent is extended or adjusted under 35 U.S.C. 154(b) by 0 days.

(21) Appl. No.: 15/307,595

(22) PCT Filed: Apr. 30, 2015

(86) PCT No.: PCT/EP2015/059589
§ 371 (c)(1),
(2) Date: Oct. 28, 2016

(87) PCT Pub. No.: WO2015/166081
PCT Pub. Date: Nov. 5, 2015

(65) Prior Publication Data
US 2017/0043063 A1  Feb. 16, 2017

(30) Foreign Application Priority Data

Apr. 30, 2014 (EP) .................................. 14166695

(51) Int. Cl.
| A61B 8/14 | (2006.01) |
| A61L 31/18 | (2006.01) |
| A61L 29/08 | (2006.01) |
| A61L 29/14 | (2006.01) |
| A61L 31/08 | (2006.01) |

(52) U.S. Cl.
CPC ............... *A61L 31/18* (2013.01); *A61L 29/08* (2013.01); *A61L 29/14* (2013.01); *A61L 31/08* (2013.01); *A61L 31/088* (2013.01); *A61L 2420/02* (2013.01)

(58) Field of Classification Search
CPC ..... A61K 9/0021; A61K 26/185; A61K 47/26
See application file for complete search history.

(56) References Cited

U.S. PATENT DOCUMENTS

| 5,081,997 A | 1/1992 | Bosley, Jr. et al. |
| 5,201,314 A | 4/1993 | Bosley et al. |
| 5,289,831 A | 3/1994 | Bosley |
| 6,749,554 B1 | 6/2004 | Snow et al. |
| 2009/0318746 A1 | 12/2009 | Thurmond, II et al. |
| 2011/0003279 A1* | 1/2011 | Patel .................. G01D 3/10 435/5 |
| 2012/0172787 A1* | 7/2012 | McClain ........ A61B 17/320725 604/22 |

FOREIGN PATENT DOCUMENTS

| EP | 0 552 924 A1 | 7/1993 |
| EP | 1 118 337 A2 | 7/2001 |
| WO | 2012/148265 A1 | 11/2012 |
| WO | WO-2012148265 A1 * | 11/2012 ............. A61B 8/481 |
| WO | 2014/070012 A1 | 5/2014 |

OTHER PUBLICATIONS

Olivier Couture et al., "A Model for Reflectivity Enhancement Due to Surface Bound Submicrometer Particles", Ultrasound in Medicine and Biology, vol. 32, No. 8, 2006, pp. 1247-1255.

Fort, Marianne, "International Search Report in PCT/EP2015/059589", dated Jun. 30, 2015, 5 pages, European Patent Office, Rijswijk, NL.

Unlisted, "Written Opinion of the International Searching Authority PCT/EP2015/059589", dated Jun. 30, 2015, 8 pages, European Patent Office, Rijswijk, NL.

* cited by examiner

*Primary Examiner* — Micah Paul Young
(74) *Attorney, Agent, or Firm* — Hoffmann & Baron, LLP

(57) ABSTRACT

The invention provides medical devices comprising improved non-uniform coatings for ultrasound detection, which provide optimal ultrasound images. Methods for preparing such devices are also provided.

16 Claims, 14 Drawing Sheets

MEDICAL DEVICES WITH NON-UNIFORM COATINGS FOR ENHANCED ECHOGENICITY

CROSS-REFERENCE TO RELATED APPLICATIONS

This application is a U.S. National Stage filing under 35 U.S.C. § 371 of International Application No. PCT/EP2015/059589, filed Apr. 30, 2015, which in turn claims priority to European Patent Application No. 14166695.8, filed Apr. 30, 2014, the entire contents of which are incorporated by reference herein.

The invention relates to the fields of medicine, physics and biotechnology.

In order to precisely locate a medical device such as for instance a needle or catheter inside a patient, ultrasound imaging is commonly used. Ultrasound imaging relies on the different ways in which sound waves are reflected from interfaces between substances. Ultrasound waves, with frequencies above the audible range of normal human hearing, typically from 20 kHz up to several gigahertz, are reflected in areas of density differences. In practice, a transducer is used that emits ultrasound waves. Some of the reflected sound waves are detected by the transducer which turns the vibrations into electrical pulses. These electrical pulses are processed and transformed into digital images.

The use of ultrasound imaging for medical devices is well known in the art. In order to enhance the quality of ultrasound images of medical devices, the surface of such a device is typically grooved or otherwise roughened, or an ultrasound coating is applied to at least part of the surface of the device. For instance, U.S. Pat. Nos. 5,289,831 and 5,081,997 describe echogenic medical devices having a surface with partially spherical indentations, or having a surface that is coated with spherically-shaped particles, which scatter an ultrasound signal. International patent application WO-A-00/51136 describes the use of gas bubbles or metal particles for enhancing an ultrasound signal. The use of an echogenic material containing cavities or gas bubbles is also described in European patent application EP-A-0624342, whereas international patent applications WO-A-98/18387 and WO-A-00/66004 describe medical instruments with bubble generating means, which produce bubbles that are visible with ultrasound. Additionally, US patent application 2004/0077948 discloses an echogenic surface having structures entrapping gas, the entrapped gas causing the device to be ultrasonically visible.

US patent application 2005/0074406 describes an ultrasound coating containing membranes encapsulating a gas-filled core. European patent application EP 1118337 and U.S. Pat. No. 6,506,156 use an echogenic layer including a polymeric matrix with a plurality of void spaces, or glass microsphere particles, or both. US patent application 2009/0318746 describes lubricious echogenic coatings containing polymeric gas/liquid containing microparticles. WO-A-2012/148265 discloses a coating for improving ultrasound visibility of a device, said coating being made of a matrix material comprising gas-filled microparticles as contrast agents. In the examples, cannulae were dip-coated with the coating. US patent application 2002/0151796 relates to echogenic devices comprising a porous polymeric material and to devices including a coating layer having porous particles.

For fluoroscopy, marker bands can be used that are short, thin-wall tubes of gold or platinum placed on the tip of a catheter shaft. Such marker bands are not suitable for ultrasound imaging.

The use of roughened surfaces in order to enhance ultrasound visibility, involves an increased risk of discomfort for the patient since a roughened surface typically requires more force to move the device inside the patient's body and gives only a limited ultrasound visibility enhancement. The use of gas bubbles for improving ultrasound visibility has the disadvantage that it is difficult to control the concentration and size of the formed bubbles, leading to variations between coatings so that it is more difficult to obtain an optimized ultrasound imaging coating.

The use of echogenic particles is, therefore, preferred. Although various alternatives for ultrasound imaging with microparticles are available, it is advantageous to improve the visibility (i.e. the accuracy) of the obtained ultrasound images. It is hence an object of the present invention to provide improved coatings for ultrasound detection. A further objective is to provide medical devices providing for better determination of their position and orientation with ultrasonography imaging. This includes providing for more precise and/or easier determination of the position and orientation in the body of the device when using ultrasonography imaging.

The present invention provides, as an aspect, the insight that an ultrasound image is improved if at least 60% of the echogenic microparticles on at least parts of medical device have a diameter of between 10 and 45 μm and the density of the echogenic microparticles on the surface of the device is between 45 and 450 particles/mm$^2$. This is for instance apparent from the Examples: when particles with a diameter of between 10 and 45 μm are used, densities of between 45 and 450 particles/mm$^2$ provide a good visibility of at least parts of the coated object, whereas lower or higher densities typically result in an image with an undesired deviation of the object size. Hence, the visibility of at least parts of the object is best when densities of between 45 and 450 particles/mm$^2$ are used. In one preferred embodiment, a medical device is at least partly coated with echogenic particles wherein at least 60% of the echogenic microparticles on a medical device have a diameter of between 22 and 45 μm, or between 25 and 45 μm, and the density of the echogenic microparticles on the surface of the device is between 45 and 450 particles/mm$^2$ or, preferably, between 60 and 450 particles/mm$^2$.

In the invention, this is applied in non-uniform coatings. The coating may comprise parts that are different from each other and/or may not cover the surface of the medical device entirely. This advantageously can provide contrast of various parts of the device in the ultrasound image, in particular between such parts. Such contrast may advantageously provide a better view of the orientation of the medical device. This can be used for improved positioning of the device. Accordingly, the coating is applied in a non-homogenous way. For example, the coating can be applied in a spatially selective manner, such that the coating does not entirely cover the surface of the device. In addition or in the alternative, different coated parts may have different ultrasound visibility. A non-uniform coating is typically non-uniform in the surface that is coplanar to the surface of the medical device. In addition, the coating may be non-uniform over its thickness, or may be uniform over its thickness.

The non-uniform aspect of the coating preferably involves a difference in echogenicity of the different coating parts, more in particular the ultrasound visibility, such as expressed as contrast-to-noise ratio (CNR). Such difference is preferably obtained by a difference involving the microparticles applied with the coating. For example, the diameter, shape and/or composition of the microparticles may vary between various parts of the coating, in addition or in the alternative, the parts may differ in the microparticle surface density on the device.

As used herein, the term "parts of the coating" or "coated parts" refers to parts of the coating that are applied on different parts of the surface of the medical device, rather than to different sub-layers of the coating. The term hence refers to surface parts of the coating. The surface parts differ in position on the surface of the medical device, and not, or not only, in position along the thickness of the coating. Typically, a part can have a surface area of at least 0.010 $mm^2$, or at least 1 $mm^2$, for instance at least 10 $mm^2$, or at least 50 $mm^2$, or at least 1 $cm^2$, or at least 50 $mm^2$; or at least one dimension of at least 0.10 mm or at least 1.0 mm or at least 10 mm. Parts with such size are relevant for ultrasound visibility, the size distinguishes from random variations in the coating.

Particle size distributions, particle densities, and other coating properties specified for at least parts of the coating accordingly refer, in case of a coating that does not cover the entire surface, preferably to the entire coating (and hence preferably to all the parts of the medical device surface that are coated with the coating). This is in particular the case for a medical device that has the coating applied on its surface in a pattern, especially a spatially selective pattern. In case of a coating that covers the entire surface of the device, or a coating that is not applied in a pattern, preferred particle size distributions, particle densities, and other coating properties specified for at least parts of the coating refer to surface parts of the coating. In this case, the variant wherein only parts of the coating have the specified properties is especially envisaged, hence wherein the coating comprises additional parts not having these properties. This likewise applies to essential and preferred particle size distributions, particle densities and other coating properties.

In case of parts of the coating that are different from each other, the parts in particular may be parts of the coating that are applied on different parts of the surface of the device. This is preferred over differences between coating layers, i.e. coating parts that are applied on the same surface but have a different position relative to the thickness of the coating.

The non-uniform aspect of the coating can be used to provide the device with a pattern that is visible in ultrasonic images of the device. A highly preferred pattern comprises coated parts with an increased or decreased echogenicity compared to adjacent coated or non-coated parts of the surface of the device, preferably in the form of strips. Such a strip may have a width of for example 0.010 mm or more, or 0.10 mm or more, 1 mm or more, 5 mm or more, 10 mm or more, for example up to 40 mm or up to 10 mm or even higher. The length of the strip is for example at least 2 times the width of the strip, for instance at least 5 times the width. In case of an elongated medical device comprising a part that is elongated along an axis, the strip may be applied for example parallel or perpendicular to said axis. In case of a medical device with a generally cylindrical part (including, but not restricted to, a stent shaft, a needle, a catheter, tube, cannula), the strip is preferably applied as a band that extends radially around the cylindrically curved surface. In such case, the width of the marker band is in axial direction of the device. Such a marker band may form an axial segment of such device part.

Preferably the coating comprises one or more parts, such as strips, with a higher ultrasound visibility than adjacent coated or non-coated parts of the surface of the medical device; preferably the strips are marker bands. Preferably the coating part has a contrast-to-noise ratio (CNR) that is at least 1.3 times higher than that of adjacent parts of the surface of the medical device, more preferably at least 1.5 times higher, or at least 1.8 times higher. The parts can for example be applied on a curved substrate.

The marker band may comprise radial segments (each covering a radial part of the device surface, such that the marker bands is not continuous around the device) and may be applied in a spiraling manner.

The marker bands of an aspect of the invention may be placed as is conventional for radio-opaque marker bands. Marker bands can for example be placed at a distance from a distal end of a device, for example at least 0.10 mm or at least 1.0 mm or 1-10 cm from the distal end. However, the distal end can also be coated, and for example a marker band can extend to the distal end or tip of a device.

In order to distinguish between different parts/locations of a medical device the ultrasound visibility can be varied. For instance, in case the medical device comprises a needle or a catheter, preferably the tip is coated with a coating with high ultrasound visibility to permit quick detection in the body. Nevertheless, high ultrasound visibility can cause overestimation of the signal and, hence, in order for the clinician to better judge the position of the needle in the body, preferably the shaft of the needle or catheter is further provided with marker bands of optimal echogenicity. This provides as advantage that the distance can be measured or estimated, the orientation of the device can be defined, and other parts of the device and surrounding tissue can be distinguished. Due to the absence of overestimation for marker bands of optimal echogenicity, the actual width of these marker bands and distance between them can exactly correspond to the distances visible in the ultrasound image. This enables accurate positioning of the device and allows spatial measurements. Likewise underestimation may occur if the echogenicity or density of particles on the surface is too low, which can also be addressed by using marker bands with optimal echogenicity and density of particles on the surface. To better discriminate between one part(s) of the device and other part(s) of the device, said part(s) preferably have a variation in ultrasound visibility. For instance the tip of a needle or catheter preferably has a high ultrasound visibility, and multiple marker bands along the shaft with each marker band decreasing in ultrasound visibility the further it is located from the tip. In order to have marker bands with clear edges (with a high contrast difference), the marker bands are preferably spaced apart by non-coated parts.

This can also be applied to other cylindrical and non-cylindrical medical devices in which one part(s) of the device needs to be discriminated from other parts of the device.

Other suitable patterns include stripes, dots, patches, a check board pattern, blocks, triangles and many others such as arrows or a grid. Such pattern can be obtained between coated and non-coated parts, between adjacent parts of the coating with different echogenic properties, between coated parts spaced by non-coated parts, and combinations thereof. A preferred example is coated areas on a ring-shaped medical device, wherein the coated areas are spaced apart by parts that are not coated. Triangles can be used on for instance a ring-shaped device. Triangles and arrows may provide as advantage that they can point in a certain direction, improving visibility of the orientation of the device.

Preferably, a medical device, preferably ultrasound responsive medical device, has a tip and the coating comprises at least two marker bands alternating with uncoated parts of the surface of the medical device and wherein adjacent marker bands have a different ultrasound visibility. Preferably the coating comprises at least three marker bands, and the marker bands are spaced apart by, and alternating with, uncoated parts of the surface. Preferably, the medical device has a shaft and a coating comprising three adjacent marker bands with an ultrasound visibility that decreases or increases from the tip along the shaft, preferably decreases from the tip along the shaft, preferably with a decreasing surface density of the microparticles. Preferably, the difference in the average surface density of the microparticles between adjacent marker bands (or any adjacent coated parts, whether or not separated by non-coated parts) is at least 10 particles/mm$^2$, more preferably at least 20 particles/mm$^2$, even more preferably at least 50 particles/mm$^2$, or at least 90 particles/mm$^2$, or at least 100 particles/mm$^2$.

Particularly preferred are marker bands with a decreasing ultrasound visibility (as CNR) from the tip along the shaft. Preferably, the three adjacent marker bands are prepared using coating formulations with different mass concentrations of microspheres. Alternatively, the maker bands can be applied with spray coating for a different time (with the same flow) or more generally, applying different amounts of coating per surface area. Preferably, marker bands are applied with decreasing microsphere concentration for adjacent marker bands in the direction from a tip along the shaft.

In a preferred medical device, the coating comprises at least a first and second part, wherein in each of said parts, the diameter of at least 60% of the microparticles is between 22 and 45 μm, or between 25 and 45 μm, and wherein the surface density of the microparticles is between 45 and 450 particles per mm$^2$ of the surface of said medical device, wherein the average surface density of the microparticles in the first part is at least 1.25 times the surface density in the second part, more preferably at least 1.5 times, even more preferably at least 2 times or at least 3 times or at least 4 times, preferably each of said part has an area of at least 0.010 mm$^2$, or at least 1.0 mm$^2$, or at least 1 cm$^2$. Average surface density herein refers to the number of particles per mm$^2$ of the surface of the medical device in the part. This can be determined by counting the number of particles in one or more sample locations in the part. In case the sample locations have different dimensions (areas), averaging is based on the area of each sample location.

In a preferred medical device, the coating comprises at least a first coated part and second coated part, wherein the average surface density of the microparticles (number particles per surface area of the device) in the first coated part differs from the average surface density of the microparticles in the second coated part, preferably, the average surface density of the microparticles in the second coated part is at least 0.1 times the average surface density of the microparticles in the first coated part, such as at least 0.2 times, at least 0.4 times, at least 0.6 times, at least 0.8 times, or at least 0.9 times the average surface density of the first coated part, especially such times higher than the average surface density of the first coated part. Preferably each of said first coated part and said second coated part has an area of at least 0.010 mm$^2$, or at least 0.10 mm$^2$, or at least 1 cm$^2$, although at least 1.0 mm$^2$ is also possible.

In a preferred medical device, the coating comprises at least a first part and a second part, optionally at least a further third part, each of said parts optionally having a surface of at least 0.010 mm$^2$ or at least 10 mm$^2$, the parts being adjacent to each other or separated by a separator, said separator selected from an uncoated part of the surface of the medical device (which is most preferred), a coating part being essentially free of microparticles and/or a coating part having a contrast-to-noise ratio lower than 1.5, preferably 1.1 or less, the first part and second part being different in at least one of, and preferably all of:

the second part having a surface density of microparticles of at least 0.1 times the surface density of microparticles of the first part, such as at least 0.2 times, at least 0.4 times, at least 0.6 times, at least 0.8 times, or at least 0.9 times the surface density of microparticles of the first part, especially such times higher than that density of the first part, the microparticles of the first part having a number average particle size at least 1.2 times higher than the microparticles of the second part, preferably at least 1.5 times higher, the second part having a surface density of particles with a diameter between 10 and 45 μm, more preferably between 22 and 45 μm, or between 25 and 45 μm, that is at least 0.1 times higher than the surface density of such particles in the first part, such as at least 0.2 times, at least 0.4 times, at least 0.6 times, at least 0.8 times, or at least 0.9 times higher than the surface density of such particles in the first part, wherein the surface density is expressed in number of particles per mm$^2$ surface of the medical device. This provides advantageously for a clear pattern in ultrasound images that can help in positioning the device in a patient.

A further preferred medical device is a device, wherein in said first coated part and the second coated part one or more of the following conditions A), B), C), D), E), and F) applies, provided that the condition for the first coated part is different from the condition for the second coated part:

A) the diameter of at least 60% of said microparticles on said medical device is between 22 and 45 μm, or between 25 and 45 μm, and wherein the density of said microparticles on the surface of said medical device is between 10 and 1800 particles/mm$^2$, preferably the density of said microparticles on the surface of said medical device is between 45 and 450 particles/mm$^2$, or B) the diameter of at least 60% of said microparticles on said medical device is between 22 and 27 μm, or between 25 and 27 μm, and wherein the density of said microparticles on the surface of said medical device is between 50 and 1800 particles/mm$^2$, preferably the density of said microparticles on the surface of said medical device is between 150 and 450 particles/mm$^2$, or C) the diameter of at least 60% of said microparticles on said medical device is between 27 and 32 μm and wherein the density of said microparticles on the surface of said medical device is between 25 and 650 particles/mm$^2$, preferably the density of said microparticles on the surface of said medical device is between 70 and 450 particles/mm$^2$, or D) the diameter of at least 60% of said microparticles on said medical device is between 32 and 38 μm and wherein the density of said microparticles on the surface of said medical device is between 50 and 275 particles/mm$^2$, preferably the density of said microparticles on the surface of said medical device is between 45 and 225 particles/mm$^2$, or E) the diameter of at least 60% of said microparticles on said medical device is between 38 and 45 μm and wherein the density of said microparticles on the surface of said medical device is between 10 and 250 particles/mm$^2$, preferably the density of said microparticles on the surface of said medical device is between 45 and 150 particles/mm², or F) the diameter of at least 60% of said microparticles on said medical device is between 45 and 53 μm and wherein the density of said microparticles on the surface of said medical device is between 10 and 200 particles/mm².

Preferably said first and second part are each a marker band on a curved surface of a shaft of a medical device, separated from each other in the axial direction of said shaft by said separator, preferably by at least 1 mm, or at least 5 mm, or at least 10 mm, in the direction of the axis of the shaft. Such separation helps in recognition of the marker bands and the orientation of the device.

Preferably, the second part has a surface density of particles with a diameter between 10 and 45 μm, more preferably between 22 and 45 μm, or between 25 and 45 μm, that is at least 0.1 times higher, such as at least 0.2 times, at least 0.4 times, at least 0.6 times, at least 0.8 times, or at least 0.9 times higher than the surface density of such particles in the first part. This provides for good contrast between the parts and hence the orientation of the device can be clearly seen in ultrasound images. All surface densities can be expressed in number of particles per mm² surface of the medical device covered by the coating or by the coating part.

As used herein, the visibility of an object as measured with ultrasound waves (also called the ultrasound visibility of an object) is defined as the accuracy with which the exact location of said object can be determined. Hence, visibility is proportional to the detail, or sharpness, of the obtained ultrasound image; the more detailed (sharper) the image, the better the user can locate the object, hence the better the visibility of the object is. Interestingly, within the tested density ranges of between 0-1800 microspheres/mm², roughly corresponding to a surface packing of between 0.1 and 100% (a surface packing of 100% meaning that the highest possible, hence complete hexagonal packing of spherical particles in a plane is achieved), it appears that objects with a surface density, and hence a reflectivity, above an optimal value lead to an overestimation of the object size under ultrasound. Hence, a higher reflectivity of ultrasound waves does not always result in a better visibility of a medical object. Contrary, the inventors have found that there is an optimal particle density, depending on the particle size. If the density becomes too high, the reflectivity will increase but the ability of a user to determine the exact location of a device will decrease because the ultrasound image will provide an overestimation of the object's size. The boundaries between the object and the environment become more vague, thereby decreasing the visibility of the object. If the particle density is too low, this may cause an underestimation of the signal and object size.

Without wishing to be bound by any theory, it is believed that as the number of particles on the surface increases, more ultrasound waves are scattered and returned to the transducer resulting in an increase of reflectivity. At low particle densities, this increase in reflectivity increases the contrast-to-noise ratio of the signal of the coated device on the ultrasound machines screen, when compared to the signal of the surrounding medium, and it also increases the sharpness of the image, resulting in an improved ultrasound image on a screen. However, when the number of particles increases beyond an optimum point, the scattering is further increased but the ultrasound image of the device becomes larger and less defined, leading to a less defined or less sharp image on the screen. This results in an overestimation of the size of the device, the appearance of ultrasound artefacts and a less defined ultrasound image for a user. The result of this is a suboptimal image of the device.

This insight of the present invention is in contrast with the general teaching in the art. For instance, Couture et al (Ultrasound in Medicine and Biology, Vol. 32, No. 8, pp. 1247-1255, 2006) describes two mathematical models to predict the signal enhancement, or reflectivity, of microparticles on a surface. In the so-called layer model, the ultrasound particles are viewed as a continuous film covering the surface, with thickness corresponding to the particle diameter. According to this model, the reflectivity depends only on the film thickness (particle size) and not the particle density. In the second mathematical model proposed in Couture et al, at low surface concentration the response to ultrasound radiation is modelled as the sum of the individual impulse response of all the particles, with all phases accounted for. From equation (5) on page 1249 of Couture et al it is clear that according to this model the reflectivity is proportional to the surface density of the ultrasound particles. Experimental data subsequently demonstrate that this is indeed the case for confluence fractions (surface packing) of up to 200% (which would roughly involve a particle density of up to 70 000 particles/mm² when the 5 μm particles of Couture et al are used). For practical reasons, such high particle densities are normally not used on medical devices because it would become problematic to bind such high amounts of particles to a surface. Hence, Couture et al only investigates the ultrasound reflectivity of echogenic particles and teaches a linear relationship between reflectivity and particle density up to 70 000 particles/mm². What is not realized in Couture et al, however, is the insight of the present invention that the amount of reflectivity of the ultrasound particles does not always correlate to the visibility of the device in a patient. The present invention provides the insight that too much reflectivity actually decreases the visibility by a loss of quality of the ultrasound image. According to the invention, if the reflectivity is too high, then signal broadening and artefacts begin to appear and the ultrasound image seen by the user becomes less detailed (less sharp). In this case the user will overestimate the size of the device and loose accuracy. The present invention therefore provides coated medical devices with an improved ultrasound visibility. The diameters and the densities of the echogenic particles are adjusted in order to obtain an ultrasound image with improved visibility, meaning that the user is capable of accurately determining the position of the device inside a body.

Accordingly, the invention provides in an aspect a medical device comprising a coating for ultrasound detection, said coating comprising microparticles that are visible with ultrasound, wherein in at least parts of the coating, the diameter of at least 60% of said microparticles on said medical device is between 10 and 45 μm and wherein the density of said microparticles on the surface of said medical device per surface area of the coating parts is between 45 and 450 particles/mm², wherein said coating is non-uniform. Hence, the medical device is at least partly coated with a coating. The coating comprises at least parts comprising ultrasound visible microparticles with a surface density between 45 and 450 particles/mm² and wherein at least 60% of the microparticles have a diameter of 10 and 45 μm. The device can optionally comprise other coated parts wherein the particles may for instance have a different diameter and/or surface density. For example the device may comprise further coating parts having from more than 450 to 1800 particles/mm² or 500 to 1800 particles/mm², or parts wherein at least 60% of the microparticles have a size of less than 10 μm or more than 45 μm, for example 1.0 to 9.0 μm or 46 to 53 μm. The device may further comprise non-coated parts (with a surface density of 0 particles/mm²).

Preferably, at least 65% of said microparticles in at least parts of the coating on said medical device have a diameter of between 10 and 45 μm. More preferably, at least 70%, or at least 75%, of said microparticles in at least parts of the coating on said medical device have a diameter of between 10 and 45 μm. More preferably, at least 80%, or at least 85%, or at least 90% of said microparticles in at least parts of the coating on said medical device have a diameter of between 10 and 45 μm. Most preferably, at least 95% of said microparticles in at least parts of the coating on said medical device have a diameter of between 10 and 45 μm. By using a high proportion of particles with a diameter between 10 and 45 μm, and a surface density of between 45 and 450 particles/mm² in at least parts of the coating, in combination with a non-uniform coating, an optimal visibility of the medical device is obtained. In one particularly preferred embodiment, a medical device is provided that comprises a coating for ultrasound detection, wherein said coating comprises at least parts of the coating comprising microparticles that are visible with ultrasound and wherein the diameter of at least 60% (preferably of at least 65%, 70%, 75%, 80%, 85%, 90% or 95%) of said microparticles on said medical device is between 22 and 45 μm, or between 25 and 45 μm, or between 20 and 25 μm, or between 25 and 40 μm, and wherein the density of said microparticles on the surface of said medical device is between 45 and 450 particles/mm² in said at least parts of the coating. In another preferred embodiment, said density is between 60 and 450 particles/mm² in at least said parts of the coating. In addition, these particles sizes and densities are preferred for the particle size distribution and density for the average of the entire coating.

Preferably, the diameter size of at least 60% of the individual particles is randomly distributed between 10 and 45 μm in at least parts of said coating. In another embodiment, the diameter size of at least 60% of the individual particles is randomly distributed between 22 and 45 μm, or between 20 and 45 μm, or between 25 and 45 μm. It is also possible to use a mixture of particles with a higher proportion of particles with a diameter size between a more narrow sub-range. For instance, one preferred embodiment provides a medical device according to the present invention, having at least parts wherein the diameter of at least 60% of said microparticles on said medical device is between 22 and 27 μm, or between 20 and 27 μm, or between 25 and 30 μm. Optionally such part has a particle density of between 50 and 450 particles/mm², or 450-1800 particles/mm² in combination with parts having a surface density of 45 to 450 particles/mm². A particle density of between 150 and 450 particles/mm² provides an optimal visibility of the part and is therefore preferred. Even more preferably, said particle density is between 150 and 300 particles/mm² for optimal visibility.

One embodiment therefore provides a medical device wherein at least parts are coated with a coating for ultrasound detection, said coating comprising microparticles that are visible with ultrasound, wherein in at least parts of the coating the diameter of at least 60% of said microparticles on said medical device is between 22 and 27 μm, or between 20 and 25 μm, or between 25 and 30 μm, and wherein the density of said microparticles on the surface of said medical device is between 50 and 450 particles/mm², or 450 to 1800 particles/mm² in combination with parts having a surface density of 45 to 450 particles/mm². Preferably between 150 and 450 particles/mm², more preferably between 150 and 300 particles/mm². Preferably, at least 65%, more preferably at least 70%, more preferably at least 75%, more preferably at least 80%, more preferably at least 85%, more preferably at least 90%, more preferably at least 95% of said microparticles on said medical device have a diameter between 22 and 27 μm, or between 25 and 30 μm, or between 20 and 25 μm.

In yet another embodiment, a medical device is at least in parts coated with a coating comprising ultrasound particles wherein the diameter of at least 60% of said microparticles on said medical device is between 27 and 32 μm. For such parts, the particle density is for example between 45 and 450 particles/mm², or 25 to 45 or 450 to 650 particles/mm². A particle density of between 70 and 450 particles/mm² is particularly preferred because a combination of a particle size of between 27 and 32 μm and a density of between 70 and 450 particles/mm² improves the visibility of the part of a medical device inside a body. Even more preferably, said particle density is between 80 and 300 particles/mm² for optimal visibility.

Further provided is therefore a medical device at least partly coated with a coating for ultrasound detection, said coating comprising microparticles that are visible with ultrasound, wherein the diameter of at least 60% of said microparticles on said medical device is between 27 and 32 μm and wherein the density of said microparticles on the surface of said medical device is between 25 to 45 or 45-450 or 450-650 particles/mm², preferably 70-450 particles/mm², more preferably 80 to 300 particles/mm² in these parts. Preferably, at least 65%, more preferably at least 70%, more preferably at least 75%, more preferably at least 80%, more preferably at least 85%, more preferably at least 90%, more preferably at least 95% of said microparticles on said medical device have a diameter between 27 and 32 μm.

In yet another embodiment, a medical device is at least partly coated with a coating comprising ultrasound particles wherein the diameter of at least 60% of said microparticles on said medical device is between 32 and 38 μm. In this case, a particle density of between 45 and 225 particles/mm² is particularly preferred because a combination of a particle size of between 32 and 38 μm and a density of between 50 and 275 particles/mm² is suitable. A density of between 45 and 225 particles/mm² particularly improves the visibility of a medical device inside a body. Further provided is therefore a medical device comprising at least parts with a coating for ultrasound detection, said coating comprising microparticles that are visible with ultrasound, wherein the diameter of at least 60% of said microparticles on said medical device is between 32 and 38 μm and wherein the density of said microparticles on the surface of said medical device is between 50 and 275 particles/mm², preferably 45 and 225 particles/mm² in these parts. Again, it is preferred that at least 65%, more preferably at least 70%, more preferably at least 75%, more preferably at least 80%, more preferably at least 85%, more preferably at least 90%, more preferably at least 95% of said microparticles on said medical device have a diameter between 27 and 32 μm in such part. By using a high proportion of particles with the recited diameters and the recited surface densities, an optimal visibility of the medical device part is obtained.

In yet another embodiment, a medical device is at least partly coated with ultrasound particles wherein the diameter of at least 60% of said microparticles on said medical device is between 38 and 45 μm in parts of the coating. In this case, a particle density of between 10 and 250 particles/mm² is suitable. A particle density of between 45 and 150 particles/mm² is particularly preferred because a combination of a particle size of between 38 and 45 µm and a density of between 45 and 150 particles/mm² in the part of the coating further improves the visibility of the device part.

Further provided is therefore a medical device comprising at least parts with a coating for ultrasound detection, said coating comprising microparticles that are visible with ultrasound, wherein the diameter of at least 60% of said microparticles on said medical device is between 38 and 45 µm and wherein the density of said microparticles on the surface of said medical device is between 45 and 150 particles/mm² in these parts. Preferably, at least 65%, more preferably at least 70%, more preferably at least 75%, more preferably at least 80%, more preferably at least 85%, more preferably at least 90%, more preferably at least 95% of said microparticles on said medical device have a diameter between 38 and 45 µm.

In yet another embodiment, a medical device has parts coated with ultrasound particles wherein the diameter of at least 60% of said microparticles on said medical device is between 45 and 53 µm. In this case, a particle density of between 10 and 200 particles/mm² is suitable to improve the visibility of the device in the part.

The insight of the present invention is in contrast with prior art teachings such as U.S. Pat. Nos. 5,289,831 and 5,081,997, which suggest that any amount of particles will provide a good image. U.S. Pat. No. 5,081,997 (column 6) and U.S. Pat. No. 5,289,831 (column 7) teach that glass microspheres with an outer diameter of about 5 microns is one acceptable option. Further, a general size range of 1-50 microns is given. US patent application 2009/0318746 discloses a preferred size range for echogenic particles of 0.1-30 µm. Furthermore, European patent application EP-A-1118337 and U.S. Pat. No. 6,506,156 describe general size ranges of 20-200 µm and 50-150 µm. Hence, according to the prior art, the size of the echogenic particles is not very critical. Furthermore, no correlation is made between the sizes of the particles and optimal particle densities, as provided by the present invention. It is this insight about the specific combinations of particle sizes and particle densities that improves the visibility of ultrasound images of medical devices in a body. The optimal density ranges and particle sizes as provided by the present invention are not disclosed nor suggested in the prior art.

A medical device according to the present invention can be coated in a non-uniform manner with a coating comprising one or more of various kinds of microparticles that are visible with ultrasound. Such microparticles are known in the art. Suitable microparticles comprise for instance, or are made from, a material selected from the group consisting of polymers, ceramics, glasses, silicates, organic materials, metals and any combination thereof. In one embodiment, solid microparticles are used. Other options include hollow microparticles filled with a fluid, preferably, gas-filled hollow microparticles. Said gas preferably comprises air, nitrogen, a noble gas, a hydrocarbon and/or a fluorinated gas. In one embodiment, air-filled particles are used. Preferably, the microparticles are essentially spherical and/or solid, especially not hollow or gas-filled, and preferably made of polymers, ceramics, glasses, silicates, organic materials, metals and any combination thereof. This can provide good echogenicity by the reflections from the surface of the particles interfacing with the matrix of the coating.

In one preferred embodiment, said echogenic microparticles are echogenic microspheres. In one embodiment, said microparticles are present in at least parts of the coating as a monolayer because this reduces the thickness and roughness of the surface, as compared to double layers and multilayers. A less roughened surface typically requires less force to move the device inside a patient's body. A thinner coating affects the properties of the medical device less. Preferably, the coating is applied in a thickness of 10 to 100 µm, more preferably 10 to 60 µm, even more preferably 20 to 50 µm.

Preferably, echogenic microparticles with a diameter between 10 and 45 µm or between 22 and 45 µm are used in at least parts of the coating, or between 20 and 45 or 25 µm, or between 25 and 45 or 30 µm. This means that at least 60%, preferably at least 65%, preferably at least 70%, preferably at least 75%, preferably at least 80%, preferably at least 85%, preferably at least 90% and most preferably at least 95% of the particles have a diameter between 10 and 45 µm or between 22 and 45 µm in at least parts of the coating, or between 20 and 45 or 25 µm, or between 25 and 45 or 30 µm. Hence, some variations are tolerated, as long as the majority of the particles have a diameter within the recited diameter range. Echogenic microparticles with a diameter between 10 and 45 µm are preferred in at least parts of the coating for coating medical devices, because significantly smaller particles have a lower ultrasound scattering capacity so that echogenicity is often not sufficiently enhanced and the contrast-to-noise ratio is often too low, whereas significantly larger particles often result in a highly increased scattering effect and therefore an overestimation of the size of the medical device. Furthermore, with particles with a diameter of 45 µm or less, a coated medical device part is typically sufficiently smooth to avoid discomfort for a subject, which would be due to resistance that is experienced when moving a device with a rough surface inside a subject's body.

A medical device is defined herein as any kind of device that can be used in an animal or human body. Said medical device can preferably be inserted or implanted in said body. Preferably such medical device is an instrument used in surgery, treatment and/or diagnosis. Surgical instruments are well known in the art. Non-limiting examples of medical devices include catheters, needles, stents, cannulas, tracheotomes, endoscopes, dilators, tubes, introducers, markers, stylets, snares, angioplasty devices, trocars and forcepses. A medical device according to the present invention is, therefore, preferably selected from the group consisting of catheters, needles, stents, cannulas, tracheotomes, endoscopes, dilators, tubes, introducers, markers, stylets, snares, angioplasty devices, fiducials, trocars and forcepses. The medical device is typically not a glass slide. Typically, the surface on which the coating is applied is not a glass surface.

As used herein, a coating for ultrasound detection comprises any coating that is tolerated by a human or animal body and that comprises microparticles that can be visualized, due to scattering of ultrasound waves. Typically, such coating comprises biocompatible materials that are non-toxic, hypoallergenic and stable.

An ultrasound wave (also called "an ultrasound signal" or "ultrasound") is defined as a sound pressure wave with a frequency above the audible range of normal human hearing. Typically, ultrasound waves have a frequency above 20 kHz. For imaging of medical devices, ultrasound waves with a frequency between 2 MHz and 50 MHz are preferably used.

As used herein, the term "ultrasound image" means any kind of visualization of an object using ultrasound waves. Typically, reflected ultrasound waves are converted into electrical pulses which are processed and transformed into digital images. Such images are embraced by the term ultrasound image.

A microparticle is defined herein as a particle with a size below 1000 µm (preferably equal to or higher than 1 µm and lower than 1000 µm). Microparticles can have any shape, such as a regular shape (for instance spherical, oval or cubical, plates, needles) or an irregular shape.

A microsphere is defined herein as an essentially spherical particle with a diameter lower than 1000 µm, preferably lower than 500 µm, typically more than 1 µm. The term "essentially spherical" reflects the fact that the particles need not be perfectly spherical as long as the distances between the centre and any point at the surface do not differ more than 50%, more preferably no more than 30%, from each other in at least 70%, preferably at least 80%, most preferably at least 90% of the particles.

Unless specified otherwise, particle sizes are measured with electron microscopy or optical microscopy. Particle sizes of particles embedded within a matrix can be determined with electron microscopy based on the cross-section. Percentages of microparticles as used in particle size distributions, refers to number %, as number of the particles, unless specified otherwise.

Surface density of the particles can be determined with optical image analysis. A random distribution of particle diameters includes a normal distribution.

A monolayer, also called a single layer, is defined herein as a one-particle thick layer of particles on the surface of a device, meaning that there is on average no more than one particle on an axis perpendicular to the surface of the device. A double layer is defined herein as a two-particle thick layer of particles on the surface of a device, meaning that there is on average no more than two particles on an axis perpendicular to the surface of the device. Echogenic microparticles are defined herein as microparticles that are able to reflect an ultrasound wave.

A diameter of a microparticle according to the invention is defined herein as the maximal size of said particle. Said particle does not need to be exactly spherical although, in practice, essentially spherical particles are preferred.

A microparticle with a diameter between a given range is defined herein as a microparticle which has a diameter which lies within the recited range, including the lower and upper value of said range. For instance, a microparticle with a diameter between 10 and 45 µm may have a diameter of 10 µm, a diameter of 45 µm, or a diameter with a value anywhere within this range.

A silicate is defined herein as any compound comprising $SiO_2$ and/or $SiO_4$ groupings, or any salt derived from the silicic acids or from silica.

As used herein, the term "glass" refers to a solid material that exhibits a glass transition when heated towards the liquid state. Preferably, silica glass is used, which is a $SiO_2$ containing glass. Typically, soda-lime-silica glass is used, which is the most prevalent type of glass. It comprises for instance $SiO_2$, sodium carbonate, calcium oxide, magnesium oxide and/or aluminium oxide. Other types of glasses can be used, such as for instance quartz, sodium borosilicate or other borosilicate glasses, lead oxide, and/or aluminosilicate.

The term "plastic" refers to organic polymers of high molecular weight. Non-limiting examples of plastics include poly(ether sulfone)s, polyisocyanates, polyurethanes, polytetrafluoroethylene, polymers or copolymers of N-vinylpyrrolidone (e.g. copolymers with butylacrylate), poly-(4-vinyl pyridine), polyacrylamide (e.g. poly(N-isopropylacrylamide)s), poly(amido-amine)s, poly(ethylene imine)s, block copolymers of ethylene oxide and propylene oxide (e.g. a poly(ethylene oxide-block-propylene oxide) or poly(ethylene oxide-block-propylene oxide-block-ethylene oxide)), block copolymers of styrene (e.g. a poly(styrene-block-isobutylene-block-styrene) or poly(hydroxystyrene-block-isobutylene-block-hydroxystyrene)), polydialkylsiloxanes, polysaccharides, polystyrenes, polyacrylates, polyalkylacrylates (e.g. a polymethylmethacrylate or a poly(2-hydroxyethylmethacrylate)), polyalkanes (e.g. polyethylene, polypropylene and polybutadiene), poly(ether ketone)s (e.g. poly(ether ketone) or poly(ether ether ketone)), polyesters (e.g. poly(ethylene terephthalate), polyglycolides, poly(trimethylene terephthalate) or poly(ethylene naphthalate), poly(lactic acid), polycapralatone, poly(butylene terephthalate), polyamides (e.g. nylon-6,6, nylon-6, a polyphthalamide or a polyaramide), and one or more combinations of the above. These can for instance be used as surface material of the medical device.

As used herein, the term "surface coverage" refers to the percentage of a surface that is covered by echogenic microparticles. The surface coverage is typically determined by dividing the added-up dimensions of microparticle-covered surface parts by the total dimension of the surface as a whole.

The term "surface density" is defined herein as the amount of particles (as number of particles) per square millimeter of the surface of a device covered by a coating part. Hence, in case of a coating part, the term refers to the number of particles per area of the surface part of the device covered by that part of the coating. The term "particle density" is used interchangeably with "surface density". In common practice, some non-significant variation between the actual density of a coated object and an indicated density value is typically allowed. For instance, a 5-10% difference is typically considered non-significant.

The term "reflectivity" as used herein typically refers to the fraction or amount of ultrasound waves returned from a surface or interface, e.g. to be received by an ultrasound transducer.

The term "contrast-to-noise ratio" (CNR) is defined herein as the difference between the reflection of a (the) echogenic particle(s) as described herein and the reflection of the surrounding tissue (background reflection). Methods for calculating CNRs are for instance disclosed in Song et al (Applied Optics, Vol. 43, No. 5 (2004); 1053-1062) and in Baldelli et al (Eur. Radiol. 19 (2009); 2275-2285)

Even more preferably, at least parts of the device have a coating wherein the surface density is lower than 150 particles/mm$^2$ and the diameter of at least 60% of the microparticles is between 38 and 45 µm. For such particles, a surface density of less than 150 particles/mm$^2$ is preferably for higher accuracy, because it provides lower risk of overestimation of the size of the device and lower risk of appearance of artefacts, compared to less-preferred embodiment of the invention with higher surface densities of such particles.

This is for instance shown in Example 5 and FIG. 9: the right image is obtained with a coated device whereby the diameter of at least 60% of the microparticles on said medical device is between 38 and 45 µm and the density of echogenic microparticles on the surface of said device is about 250 particles/mm$^2$, the middle image is obtained with a coated device with the same kind and size of particles whereby the density of echogenic microparticles on the surface of said device is about 180 particles/mm$^2$ and the left image is obtained with a coated device with the same kind and size of particles whereby the density of echogenic microparticles on the surface of said device is about 130 particles/mm$^2$. It is clear that the right image of FIG. 9 has a lower detail (sharpness), so that it is for instance less easy for a surgeon to exactly locate the end or tip of such device. Moreover, a cloud can be seen at the left end of the device, which is not especially preferred in view of quality and accuracy of the obtained image. Furthermore, a comparison between the left image of FIG. 9 (coating with a density of echogenic particles of about 130 particles/mm$^2$) and the middle image of FIG. 9 (coating with a density of echogenic particles of about 180 particles/mm$^2$) shows that the detail (sharpness) and, hence, the visibility of the left image of FIG. 9 is better than the detail (sharpness) of the middle image of FIG. 9. Example 5 and FIG. 9 show the aspect of the invention relating to the preferred particle size distribution and surface density.

Again, contrary to expectations, the present invention provides the insight that the presence of more echogenic microparticles, resulting in more reflectivity, does not always increase the visibility of a device. On the contrary, visibility is less good if densities above an optimum value are used. Locating the end or tip of such device can be improved with for example a marker band in the coating, or applying the coating in some other non-uniform way.

In one embodiment, a medical device according to the present invention comprises a plastic surface. Accordingly, the medical device surface that acts as substrate for the coating preferably comprises a polymeric/plastic material. Non-limiting examples are polymeric materials (plastics) selected from the group consisting of polyurethane, polyvinyl chloride and silicones, and PEBAX (polyether block amide). A medical device according to the present invention may also comprises a metal surface (including alloys), such as for instance stainless steel, Nitinol (metal alloy of nickel and titanium), chromium, gold, or platinum.

As stated before, suitable microparticles for a medical device according to the invention preferably comprise, more preferably are for instance made from, a material selected from the group consisting of polymers, ceramics, glasses, silicates, organic materials, metals and any combination thereof. Preferably, glass or silicate microparticles are used. In one particularly preferred embodiment, said microparticles are echogenic microspheres. Said microparticles may be solid microparticles. Hollow microparticles are also suitable, in particular gas-filled microparticles or microspheres such as gas-filled glass or silicate particles. In one embodiment, said particles are filled with air, nitrogen, a noble gas, a hydrocarbon and/or a fluorinated gas. Preferably, said particles are filled with air or a fluorinated gas.

In principle, any coating capable of applying microparticles to a medical device and that is suitable for in vivo use is suitable for a medical device according to the present invention. Such coating is preferably non-toxic, hypo-allergenic and stable. The coating typically comprises a matrix material in which the particles are embedded. The matrix material preferably comprises a polymeric component, preferably a polymeric component selected from the group consisting of a poly(ether sulfone); a polyisocyanate; a polyurethane; a polytetrafluoroethylene; a polymer or copolymer of N-vinyl-pyrrolidone such as a copolymer with butylacrylate; a poly(4-vinyl pyridine); a polyacrylamide such as poly(N-isopropylacrylamide); a poly(amido-amine); a poly(ethylene imine); a block copolymer of ethylene oxide and propylene oxide such as a poly(ethylene oxide-block-propylene oxide) or a poly(ethylene oxide-block-propylene oxide-block-ethylene oxide); a block copolymer or styrene such as poly(styrene-block-isobutylene-block-styrene) or poly(hydroxystyrene-block-isobutylene-block-hydroxystyrene); a polydialkylsiloxane; a polysaccharide; a polystyrene, a polyacrylate, a polyalkane such as polyethylene, polypropylene or polybutadiene, a poly(ether ketone) such as poly(ether ketone), poly(ether ether ketone), polyesters such as poly(ethylene terephthalate), polyglycolide, poly(trimethylene terephthalate), poly(ethylene naphthalate), poly(lactic acid), polycaprolactone, poly(butylene terephthalate), polyamides such as nylon-6,6, nylon-6, polyphthalamides or polyaramides, a polyalkylmethacrylate such as a polymethylmethacrylate, a poly(2-hydroxyethylmethacrylate), polyvinyl ethers, and combinations thereof, most preferably selected from poly(ether sulfones), polyurethanes, polyacrylates, polymethacrylates, polyamides, polycarbonates, and combinations thereof.

In one embodiment a medical device according to the invention comprises a plastic tube. Such device for instance comprises a catheter.

In a further aspect, the invention is directed to methods for preparing a medical device according to the present invention. Methods for preparing echogenic coatings and for applying these coatings on medical devices are well known in the art. For instance, known techniques for preparing polymer microcapsules are solvent evaporation, coacervation, interfacial polymerization, spray drying and fluid bed coating. Glass microcapsules can for instance prepared using ultrasonic spray pyrolysis, sol-gel processing, liquid drop processing or electrodispersion precipitation. Subsequently, a medical device is for instance coated with the microparticles by dip coating, spray coating, pad printing, roller coating, printing, painting or inkjet printing. A mask can be used to obtain a non-uniform coating. For example, a mask layer can be applied on a substrate, the masked substrate can be subjected to dip-coating, such that coating adheres to the exposed parts of the substrate (which are not covered by the mask), and the mask can then be removed. Another option includes subjecting the substrate to a pre-treatment that provides the substrate surface with a pattern that is then translated into a selective coverage of the coating. For example, the pattern can involve rendering selected parts of the surface hydrophobic and thereafter applying a water-based coating, such that the hydrophobic surface parts are not covered. Printing, pad printing (including stamping), inkjet printing, and painting can for example also be used to provide the coating as, or with, a pattern, in particular for patterns with a fine detail. Roller coating is suitable for example for applying bands of the coating.

Reference is for instance made to U.S. Pat. Nos. 5,289,831, 5,921,933, and 6,506,156, to international patent application WO-A-2007/089761 and to Ultrasound in Medicine and Biology, Vol. 32, No. 8, pp. 1247-1255, 2006, which describe methods for preparing echogenic particles and coatings. Such coating is preferably biocompatible, non-toxic, hypo-allergenic and stable. A medical device according to the invention preferably comprises a coating which comprises a matrix material listed herein before, comprising echogenic microparticles according to the present invention.

One aspect therefore provides a method for preparing a medical device comprising a non-uniform coating for ultrasound detection, said coating comprising microparticles that are visible with ultrasound, wherein in at least part of said coating, the diameter of at least 60% of said microparticles on said medical device is between 10 and 45 μm and wherein the density of said microparticles on the surface of said medical device is between 45 and 450 particles/mm$^2$, the method comprising:

providing a medical device, and coating said device with a non-uniform coating comprising microparticles that are visible with ultrasound, such that in at least part of said coating the diameter of at least 60% of said microparticles is between 10 and 45 μm and the density of said microparticles on the surface of said medical device is between 45 and 450 particles/mm².

Preferably, in at least part of said coating, at least 60%, more preferably at least 65%, more preferably 75%, more preferably at least 80%, more preferably at least 85%, more preferably at least 90%, more preferably at least 95% of said microparticles on said medical device have a diameter between 10 and 45 μm.

Also provided is a method for preparing a medical device comprising a non-uniform coating for ultrasound detection, said coating comprising microparticles that are visible with ultrasound, wherein in at least part of said coating the diameter of at least 60% of said microparticles is between 22 and 45 μm, or between 20 and 45 or 25 μm, or between 25 and 45 or 30 μm, and the density of said microparticles on the surface of said medical device is between 45 and 450 particles/mm², the method comprising:

providing a medical device, and coating said device with a non-uniform coating comprising microparticles that are visible with ultrasound, such that in at least part of said coating the diameter of at least 60% of said microparticles on said medical device is between 22 and 45 μm, or between 20 and 45 or 25 μm, or between 25 and 45 or 30 μm, and the density of said microparticles on the surface of said medical device is between 45 and 450 particles/mm². In one preferred embodiment, said device is coated with microparticles that are visible with ultrasound, such that in at least part of said coating the diameter of at least 60% of said microparticles on said medical device is between 22 and 45 μm, or between 20 and 45 or 25 μm, or between 25 and 45 or 30 μm, and the density of said microparticles on the surface of said medical device is between 60 and 450 particles/mm².

Preferably, in at least part of said coating at least 60%, more preferably at least 65%, more preferably 75%, more preferably at least 80%, more preferably at least 85%, more preferably at least 90%, more preferably at least 95% of said microparticles on said medical device have a diameter between 22 and 45 μm, or between 20 and 45 or 25 μm, or between 25 and 45 or 30 μm.

In one embodiment, in at least part of the coating, the diameter size of at least 60% of the individual particles is randomly distributed between 10 and 45 μm. In another embodiment, in at least part of the coating, the diameter size of at least 60% of the individual particles is randomly distributed between 22 and 45 μm or between 20 and 45 or 25 μm, or between 25 and 45 or 30 μm. It is also possible to use a mixture of particles with a higher proportion of particles with a diameter size within a more narrow sub-range. For instance, one preferred embodiment provides a medical device according to the present invention, wherein in at least part of the coating, the diameter of at least 60% of said microparticles on said medical device is between 22 and 27 μm or between 20 and 45 or 25 μm, or between 25 and 45 or 30 μm. In such case, a particle density of between 150 and 450 particles/mm² in at least part of the coating is preferred for providing a particularly good visibility of the part of the medical device. Even more preferred is a particle density of between 150 and 300 particles/mm² in at least part of the coating.

One embodiment therefore provides a method for preparing a medical device comprising a non-uniform coating for ultrasound detection, said coating comprising microparticles that are visible with ultrasound, wherein in at least part of the coating the diameter of at least 60% of said microparticles on said medical device is between 22 and 27 μm, or between 20 and 25 μm or between 25 and 30 and the density of said microparticles on the surface of said medical device is between 150 and 450 particles/mm², preferably between 150 and 300 particles/mm², the method comprising:

providing a medical device, and coating said device with a non-uniform coating comprising microparticles that are visible with ultrasound, such that in at least part of the coating the diameter of at least 60% of said microparticles on said medical device is between 22 and 27 μm, or between 20 and 25 μm, or between 25 and 30 μm, and the density of said microparticles on the surface of said medical device is between 150 and 450 particles/mm², preferably between 150 and 300 particles/mm².

Preferably, at least 65%, more preferably at least 70%, more preferably at least 75%, more preferably at least 80%, more preferably at least 85%, more preferably at least 90%, more preferably at least 95% of said microparticles on said medical device have a diameter between 22 and 27 μm, or between 20 and 25 μm or between 25 and 30 μm, in at least part of the coating.

In yet another embodiment, a medical device is non-uniform coated with ultrasound particles wherein in at least part of the coating the diameter of at least 60% of said microparticles on said medical device is between 27 and 32 μm. In this case, a particle density of between 70 and 450 particles/mm² is particularly preferred because a combination of a particle size of between 27 and 32 μm and a density of between 70 and 450 particles/mm² improves the visibility of a device inside a body. Even more preferably, said particle density is between 80 and 300 particles/mm² for optimal visibility in at least part of the coating.

Further provided is therefore a method for preparing a medical device comprising a non-uniform coating for ultrasound detection, said coating comprising microparticles that are visible with ultrasound, wherein in at least part of the coating, the diameter of at least 60% of said microparticles on said medical device is between 27 and 32 μm and the density of said microparticles on the surface of said medical device is between 70 and 450 particles/mm², preferably between 80 and 300 particles/mm², the method comprising:

providing a medical device, and coating said device with a non-uniform coating comprising microparticles that are visible with ultrasound, such that in at least part of the coating the diameter of at least 60% of said microparticles on said medical device is between 27 and 32 μm and the density of said microparticles on the surface of said medical device is between 70 and 450 particles/mm², preferably between 80 and 300 particles/mm². Preferably, at least 65%, more preferably at least 70%, more preferably at least 75%, more preferably at least 80%, more preferably at least 85%, more preferably at least 90%, more preferably at least 95% of said microparticles on said medical device have a diameter between 27 and 32 μm.

In yet another embodiment, a medical device is non-uniform coated with ultrasound particles wherein in at least part of the coating, the diameter of at least 60% of said microparticles on said medical device is between 32 and 38 μm. In this case, a particle density of between 45 and 225 particles/mm² is particularly preferred because a combination of a particle size of between 32 and 38 μm and a density of between 45 and 225 particles/mm² improves the visibility of a medical device inside a body. Further provided is therefore a method for preparing a medical device comprising a non-uniform coating for ultrasound detection, said coating comprising microparticles that are visible with ultrasound, wherein in at least part of the coating the diameter of at least 60% of said microparticles on said medical device is between 32 and 38 µm and the density of said microparticles on the surface of said medical device is between 45 and 225 particles/mm$^2$, the method comprising:

provide a medical device, and coating said device with a non-uniform coating comprising microparticles that are visible with ultrasound, such that in at least part of said coating, the diameter of at least 60% of said microparticles on said medical device is between 32 and 38 µm and the density of said microparticles on the surface of said medical device is between 45 and 225 particles/mm$^2$. Preferably, at least 65%, more preferably at least 70%, more preferably at least 75%, more preferably at least 80%, more preferably at least 85%, more preferably at least 90%, more preferably at least 95% of said microparticles on said medical device have a diameter between 32 and 38 µm.

In yet another embodiment, a medical device is non-uniform coated with ultrasound particles wherein in at least part of the coating, the diameter of at least 60% of said microparticles on said medical device is between 38 and 45 µm. In this case, a particle density of between 45 and 150 particles/mm$^2$ is particularly preferred because a combination of a particle size of between 38 and 45 µm and a density of between 45 and 150 particles/mm$^2$ improves the visibility of the device even more.

Further provided is therefore a method for preparing a medical device comprising a non-uniform coating for ultrasound detection, said coating comprising microparticles that are visible with ultrasound, wherein in at least part of the coating, the diameter of at least 60% of said microparticles on said medical device is between 38 and 45 µm and wherein the density of said microparticles on the surface of said medical device is between 45 and 150 particles/mm$^2$, the method comprising:

providing a medical device, and coating said device with a non-uniform coating comprising microparticles that are visible with ultrasound, such that in at least part of said coating the diameter of at least 60% of said microparticles on said medical device is between 38 and 45 µm and the density of said microparticles on the surface of said medical device is between 45 and 150 particles/mm$^2$.

Preferably, in at least part of said coating, at least 65%, more preferably at least 70%, more preferably at least 75%, more preferably at least 80%, more preferably at least 85%, more preferably at least 90%, more preferably at least 95% of said microparticles on said medical device have a diameter between 38 and 45 µm.

The invention also relates generally to a coating applied on an article, the coating comprising microparticles that are visible with ultrasound, wherein in at least parts of the coating, the diameter of at least 60% of said microparticles is between 10 and 45 µm and the density of said microparticles per surface area of the article is between 45 and 450 particles/mm$^2$. The invention also relates to use of the coating for ultrasound imaging of a coated article. The invention also relates to a coated article coated with the coating. The article can for instance be a device, such as a medical device. Preferably, said coating is non-uniform on said article. The preferred features of coatings for medical devices apply to coated articles other than medical devices as well. The invention is further illustrated by the following examples. These examples are not limiting the invention in any way, but merely serve to clarify the invention.

BRIEF DESCRIPTION OF THE DRAWINGS

FIG. 12 schematically shows some exemplary embodiments of a device according to the invention.

EXAMPLES

Examples 1-7 show in particular the effect of the particle size distribution and the particle density. These can be combined with the non-uniform coating patterns as described herein.

Example 1

Commercially available solid glass microspheres (from Cospheric) with diameters ranging from 10 to 22 µm, 22 to 27 μm, 27 to 32 μm, 32 to 38 μm, 38 to 45 μm and 45 to 53 μm, all with a density of 2.5 g/mL, were mixed through a polyurethane coating matrix. The microspheres were added in different amounts in order to prepare mixtures containing 0.5 to 75.0 vol. % microspheres in the coating matrix. Subsequently, either 30 or 60 μm thick coating films were drawn on both glass and PEBAX 6233 slides as substrates using a film applicator. The density of microspheres was determined to vary from 2 to 1831 particles/mm².

The coated substrates were measured by ultrasound using a 33 mm linear array probe operating in brightness-mode (B-mode) at 6 MHz. The substrates were placed under an approximate angle of 45 degrees inside a commercially available ultrasound phantom which acted as the medium.

From the recorded images the contrast-to-noise ratio (CNR) was determined by comparing the average pixel intensity and standard deviation of the coated objects to the values obtained for the surrounding medium, according to:

$$CNR = \frac{P_{ROI} - P_{medium}}{\sqrt{\frac{\sigma_{ROI}^2 + \sigma_{medium}^2}{2}}}$$

where $P_{ROI}$=average pixel intensity of region of interest; $P_{medium}$=average pixel intensity of medium; $\sigma_{ROI}$=standard deviation in region of interest; $\sigma_{medium}$=standard deviation in medium.

Figure 1:
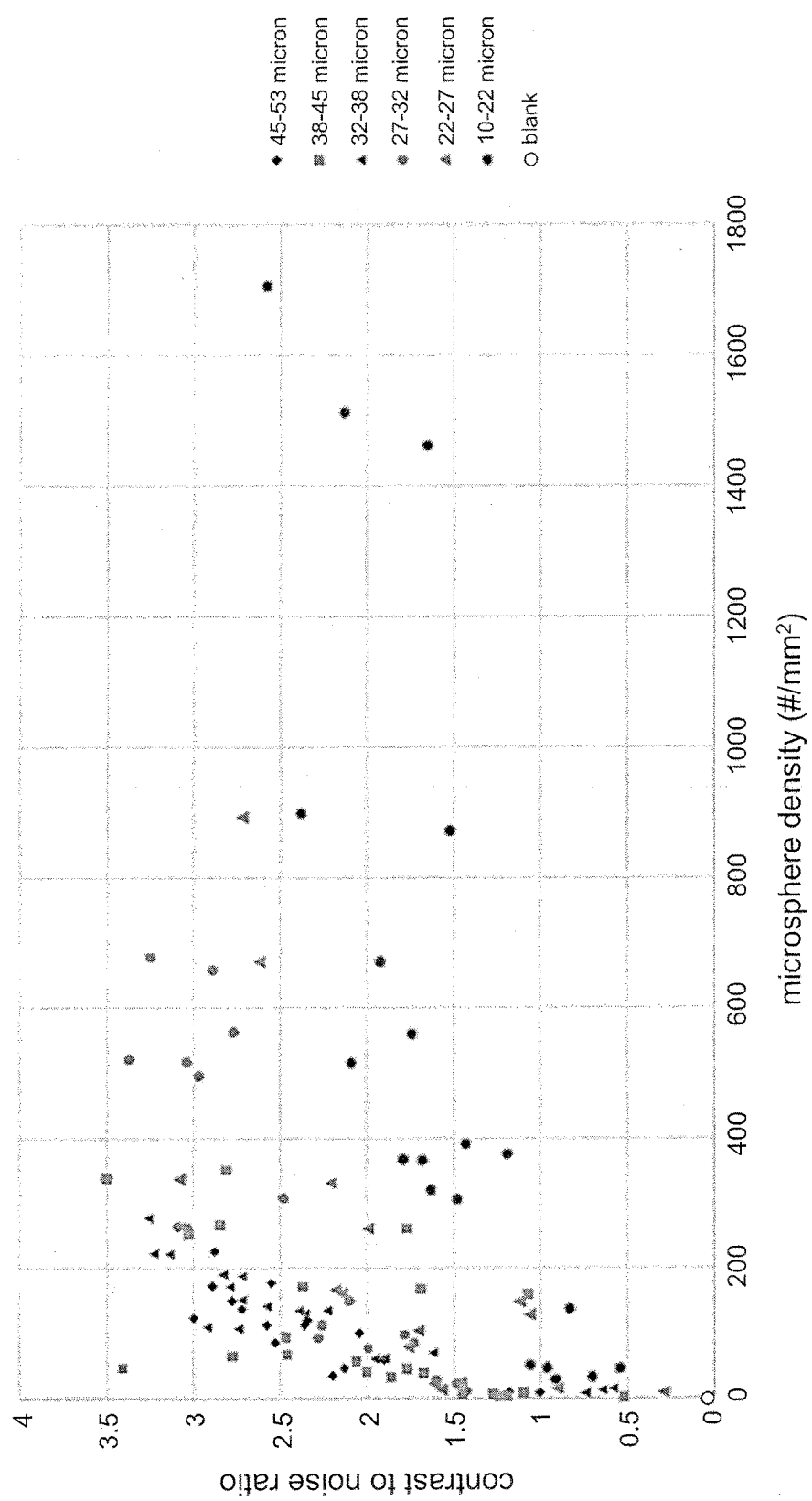
FIG. 1: Plot of the CNR against the microsphere density on the surface for different microsphere sizes.

The determined CNRs were plotted against the microsphere density in particles/mm² (FIG. 1). As can be seen in FIG. 1, the CNR approaches a value of approximately 3.5 with an increasing amount of microspheres on the surface. For approximately 2.5. Higher CNR values could not be obtained due to the fact that the complete surface is covered with glass microspheres. Adding a second layer of microspheres on top did not result in an increase of the CNR. Therefore, particles with a diameter between 22 and 45 μm are more preferred.

Example 2

Commercially available solid glass microspheres with diameters ranging from 10 to 22 μm, 22 to 27 μm, 27 to 32 μm, 32 to 38 μm, 38 to 45 μm and 45 to 53 μm, all with a density of 2.5 g/mL, were mixed through a polyurethane coating matrix. The microspheres were added in different amounts in order to prepare mixtures containing 1.0 to 75.0 vol. % microspheres in the coating matrix. Subsequently, either 30 or 60 μm thick test strip of coating was drawn on glass slides using a film applicator. These test strips were applied by masking the area which was required to be uncoated. The width of the test strips was measured.

The coated substrates were measured by ultrasound using a 33 mm linear array probe operating in brightness-mode (B-mode) at 6 MHz. The substrates were placed under an approximate angle of 45 degrees inside a commercially available ultrasound phantom which acted as the medium.

From the recorded images, the width of the test strips as visible under ultrasound was determined. The under or overestimation of the width of the test strips under ultrasound is expressed as:

$$US \text{ estimation error} = \frac{L_{US} - L_{actual}}{L_{actual}} \times 100\% \quad (1)$$

where $L_{US}$=the width of the ultrasound signal stemming from the test strips and $L_{actual}$=the actual width of the test strips.

In principle, a US estimation error of below 10% is considered acceptable. Preferably, said US estimation error is between 0 and about 5%.

Figure 2:
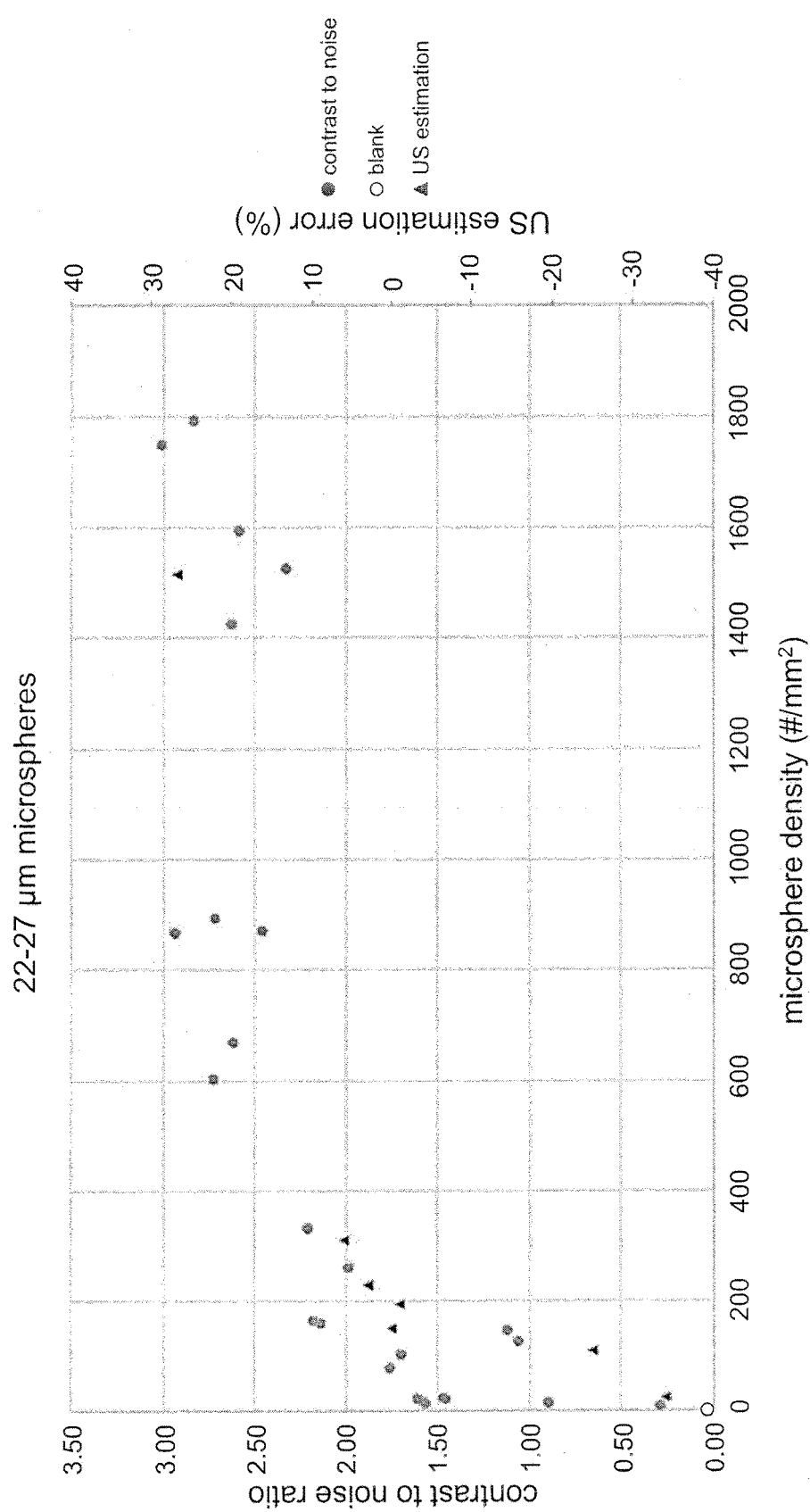
FIG. 2: for microspheres with a diameter between 22 and 27 µm, the CNR is plotted against the microsphere density, along with the US estimation error on the secondary y-axis.

In FIG. 2, for microspheres with a diameter between 22 and 27 μm, the CNR is plotted against the microsphere density, along with the US estimation error on the secondary y-axis. As can be seen in FIG. 2, the optimum range for these microspheres is lying between 150 and 450 particles/mm². Less microspheres on the surface leads to an underestimation of the width of the test strips, whereas above the upper limit overestimation of the width occurs. The most optimal range for these microspheres is lying between 150 and 300 particles/mm².

In this fashion the optimum microsphere density for each size range was established.

Figure 3:
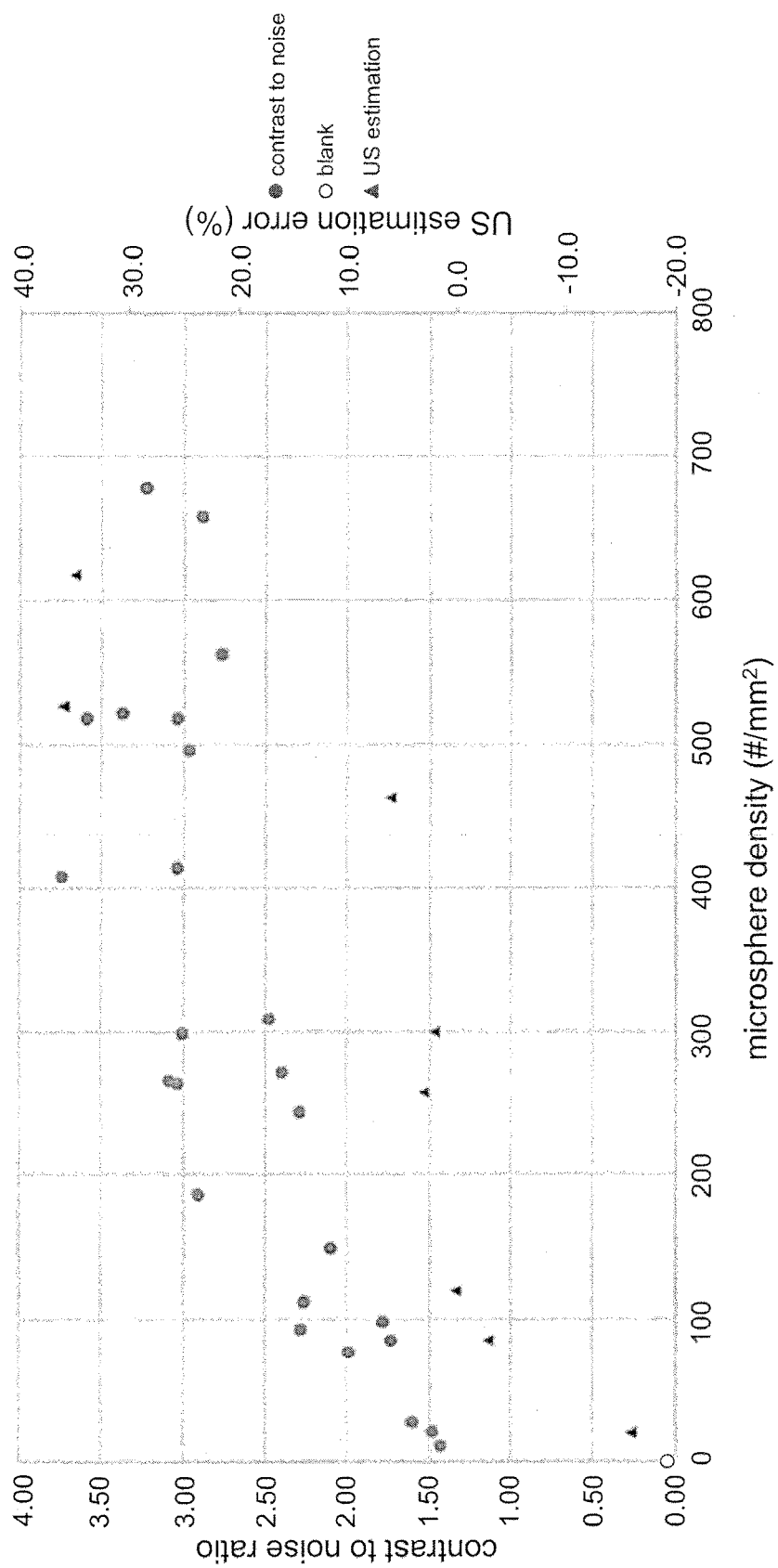
FIG. 3: for microspheres with a diameter between 27 and 32 µm, the CNR is plotted against the microsphere density, along with the US estimation error on the secondary y-axis.

In FIG. 3, for microspheres with a diameter between 27 and 32 μm, the CNR is plotted against the microsphere density, along with the US estimation error on the secondary y-axis. As can be seen in FIG. 3, the optimum range for these microspheres is lying between 70 and 450 particles/mm². Less microspheres on the surface leads to an underestimation of the width of the test strips, whereas above the upper limit overestimation of the width occurs. A particular optimal range for these microspheres is lying between 80 and 300 particles/mm².

Figure 4:
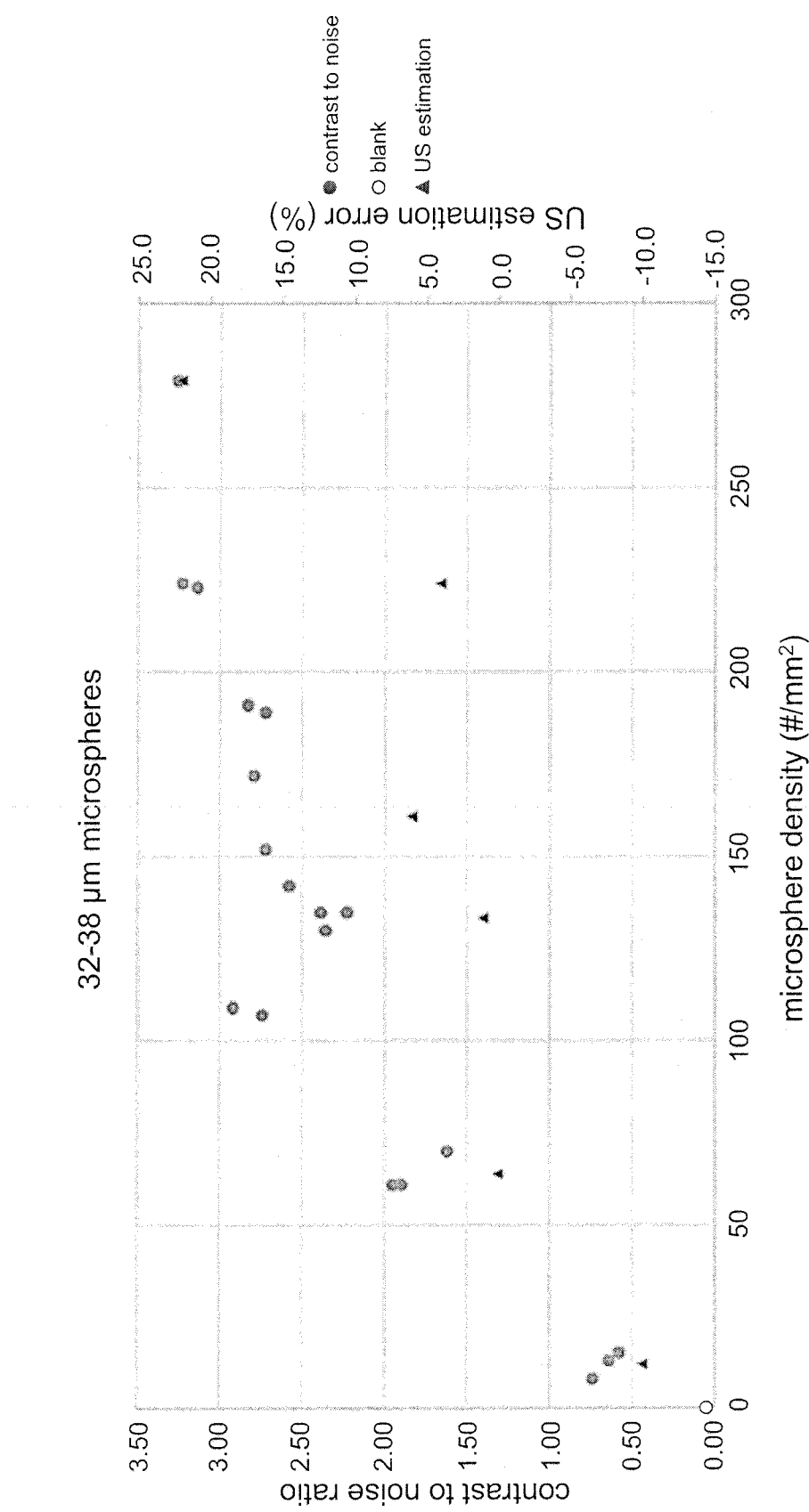
FIG. 4: for microspheres with a diameter between 32 and 38 µm, the CNR is plotted against the microsphere density, along with the US estimation error on the secondary y-axis.

In FIG. 4, for microspheres with a diameter between 32 and 38 μm, the CNR is plotted against the microsphere density, along with the US estimation error on the secondary y-axis. As can be seen in FIG. 4, the optimum range for these microspheres is lying between 45 and 225 particles/mm². Less microspheres on the surface leads to an underestimation of the width of the test strips, whereas above the upper limit overestimation of the width occurs.

Figure 5:
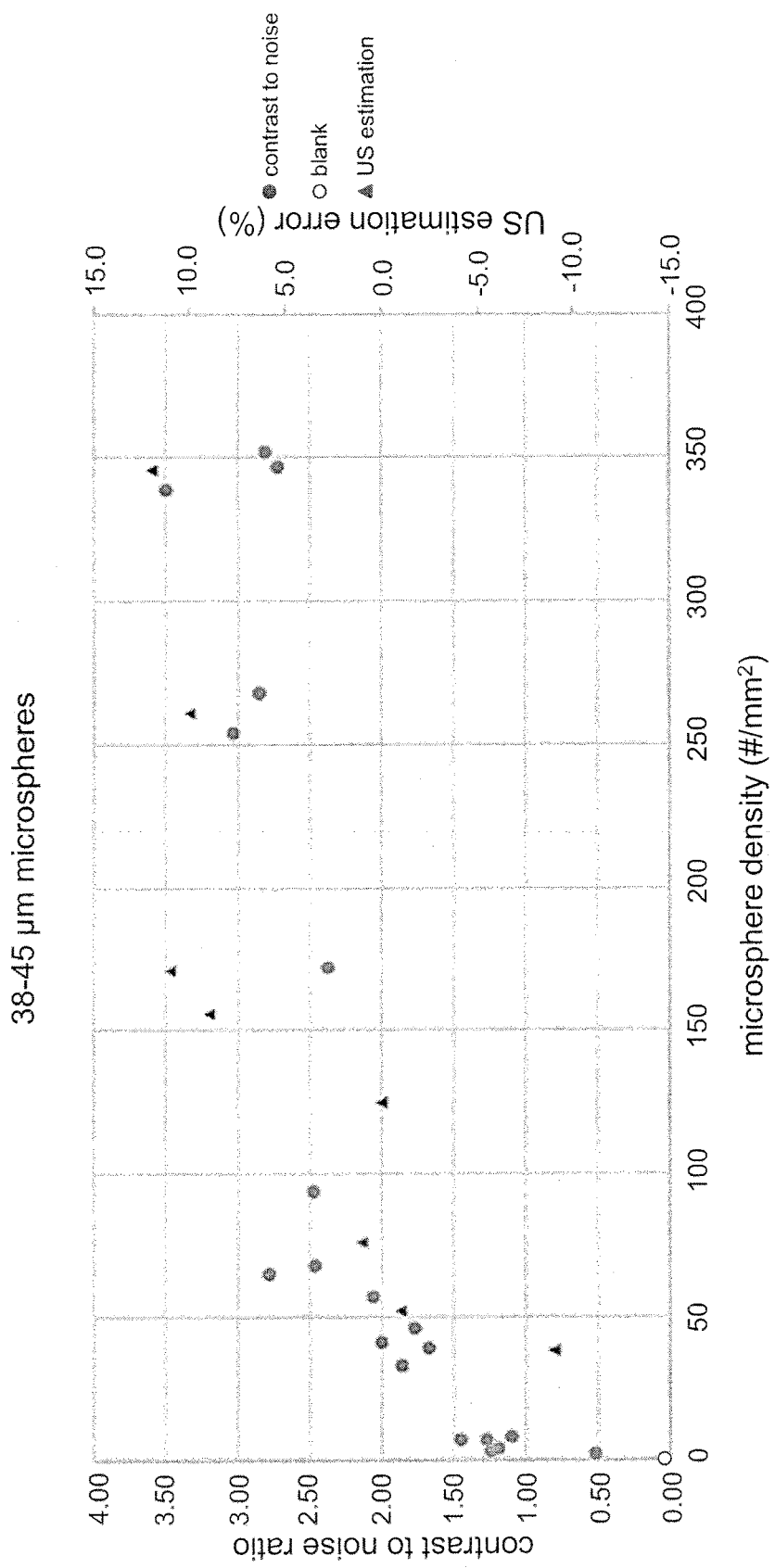
FIG. 5: for microspheres with a diameter between 38 and 45 µm, the CNR is plotted against the microsphere density, along with the US estimation error on the secondary y-axis.

In FIG. 5, for microspheres with a diameter between 38 and 45 μm, the CNR is plotted against the microsphere density, along with the US estimation error on the secondary y-axis. As can be seen in FIG. 5, the optimum range for these microspheres is lying between 45 and 150 particles/mm². Less microspheres on the surface leads to an underestimation of the width of the test strips, whereas above the upper limit overestimation of the width occurs.

Figure 6:
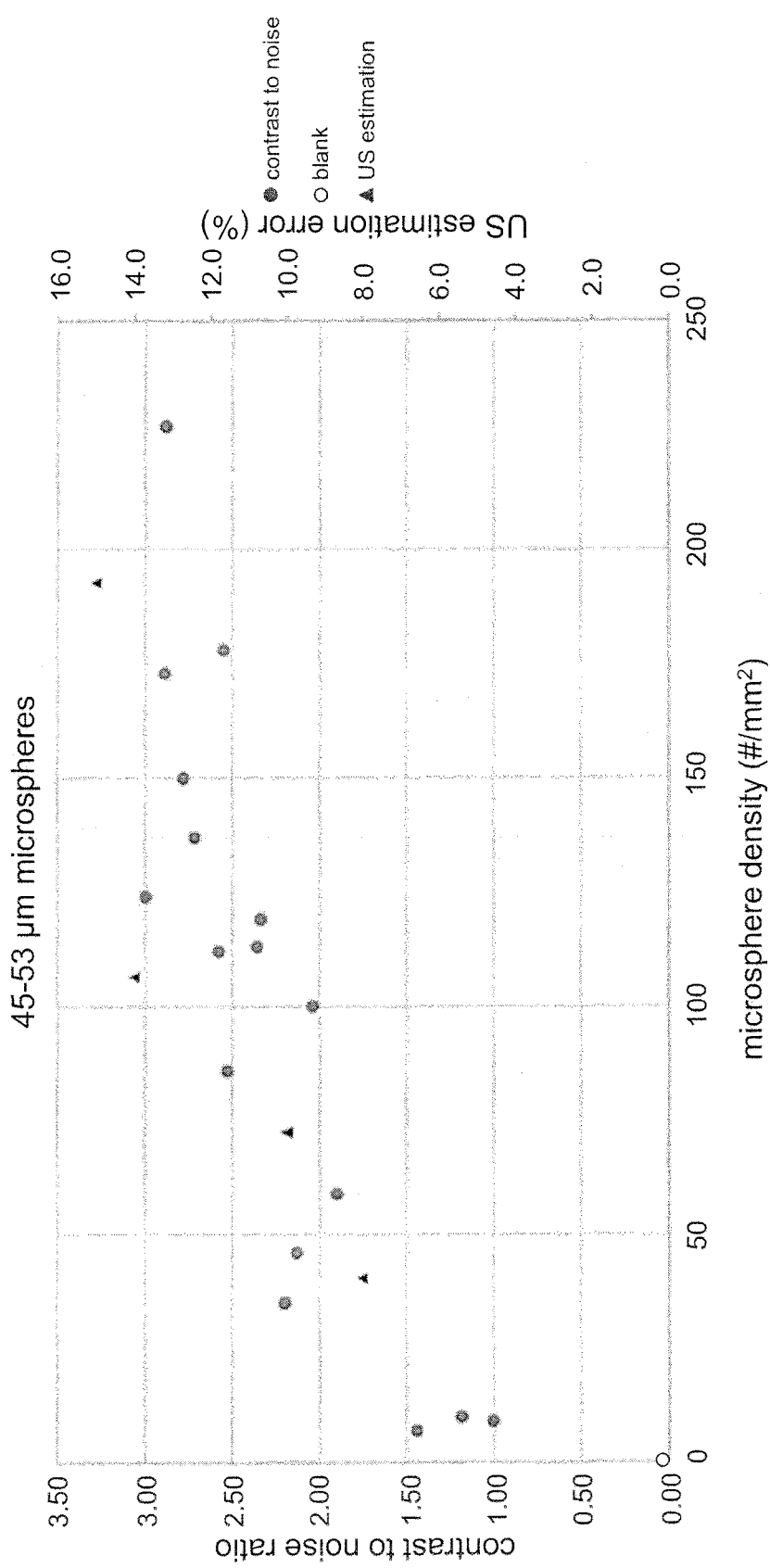
FIG. 6: for microspheres with a diameter between 45 and 53 µm, the CNR is plotted against the microsphere density, along with the US estimation error on the secondary y-axis.

For microspheres with diameters between 45 and 53 μm, on the other hand, no optimum particle density was found because overestimation of the width of the test strips is manifested over the complete range of particle density (FIG. 6).

Example 3

Solid glass microspheres with a diameter ranging from 38 to 45 μm, as described above, with a density of 2.5 g/mL, were mixed through a polyurethane coating matrix. Subsequently, glass slides and plastic (PEBAX 6233) were coated with these particles in different densities. The coated substrates were measured by ultrasound using a 33 mm linear array probe operating in brightness-mode (B-mode) at 6 MHz. The substrates were placed under an approximate angle of 45 degrees inside a commercially available ultrasound phantom which acted as the medium. From the recorded images the contrast-to-noise ratio (CNR) was determined in the same way as described in Example 1, and the determined CNRs were plotted against the microsphere concentration (FIG. 7).

Figure 7:
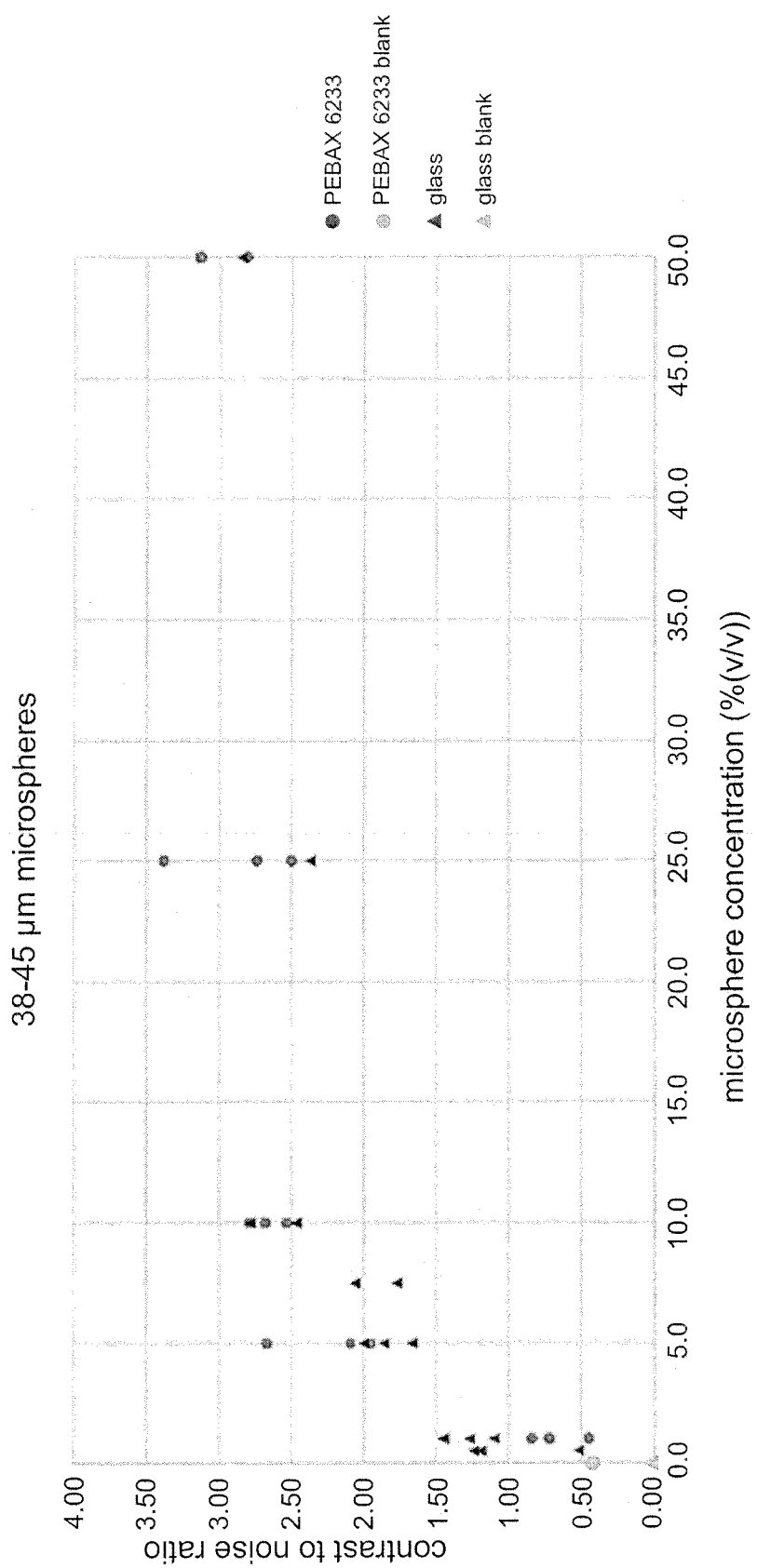
FIG. 7: CNR values for glass and plastic surfaces coated with solid glass microspheres with a diameter ranging from 38 to 45 µm.

As can be seen in FIG. 7, the CNR values for glass and plastic coated with the same amount of particles are comparable. This demonstrates that the material of the used surfaces does not significantly affect the CNRs.

Example 4

Example 1 was repeated with the solid glass microspheres with a diameter ranging from 22 to 27 µm, as described above, and with hollow glass microspheres with diameter ranging from 25 to 27 µm and densities of 0.14 g/mL and 0.46 g/mL. Glass slides were coated with these particles in different densities. The coated substrates were measured by ultrasound using a 33 mm linear array probe operating in brightness-mode (B-mode) at 6 MHz. The substrates were placed under an approximate angle of 45 degrees inside a commercially available ultrasound phantom which acted as the medium. From the recorded images the contrast-to-noise ratio (CNR) was determined in the same way as described in Example 1, and the determined CNRs were plotted against the microsphere concentration (FIG. 8).

Figure 8:
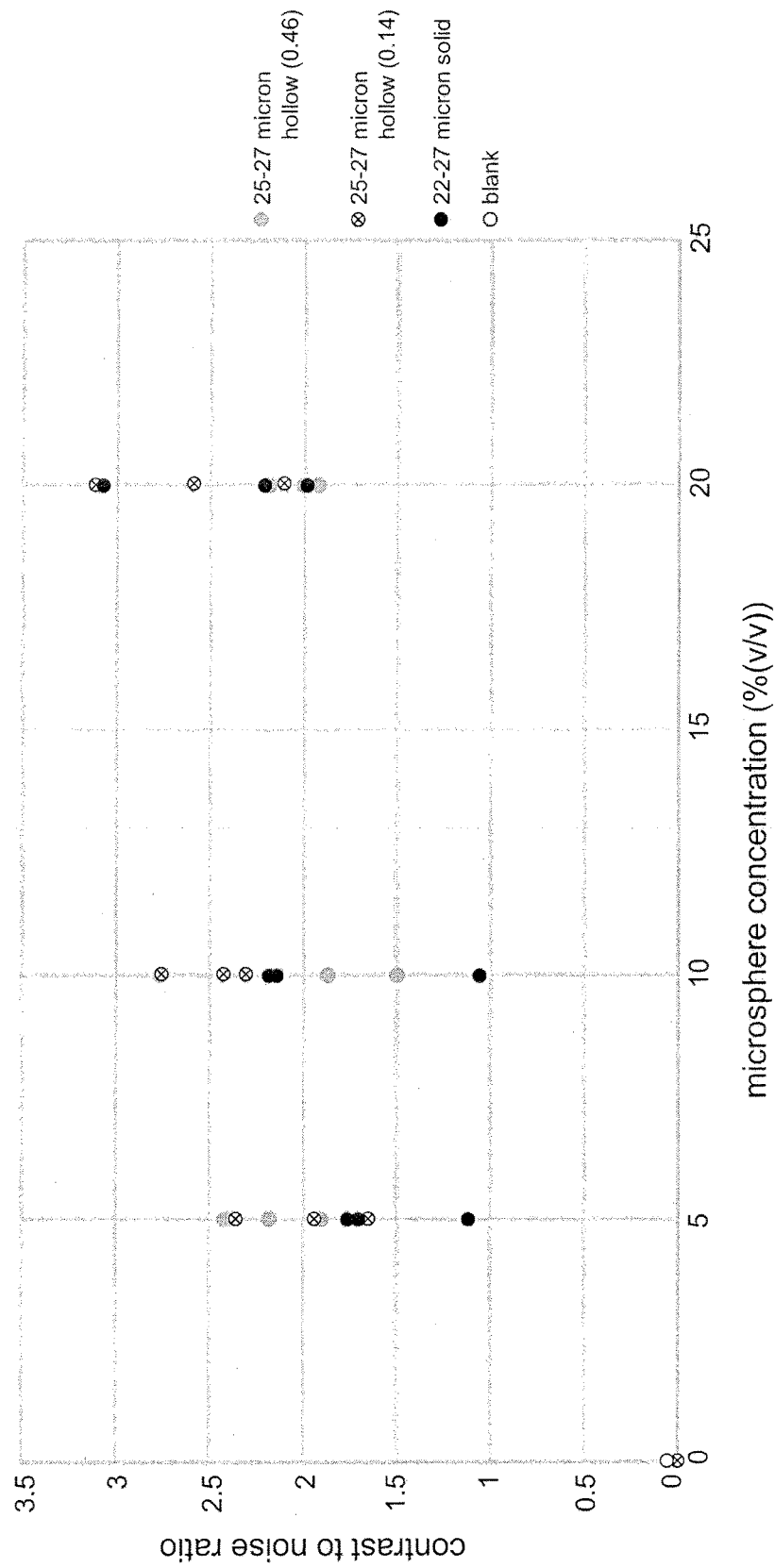
FIG. 8: CNR values for glass slides coated with solid glass microparticles and hollow glass microparticles.

As can be seen in FIG. 8, the CNR values for the solid and hollow particles are comparable, meaning that both solid and hollow particles are suitable for improving the visibility of a medical device according to the present invention.

Example 5

Commercially available air-filled glass microspheres (from Cospheric) with diameters between 38 and 45 µm and a density of 0.46 g/mL were mixed through a coating matrix, Labo coat, which is commercially available from Labo Groep (Tilburg, The Netherlands). The microspheres were added in different amounts in order to prepare mixtures containing 2.0, 3.0 and 4.0 wt. % microspheres in the coating matrix. The coating was applied by dip coating on polyurethane tubes, resulting in coated tubes with a microsphere density of about 130 particles/mm² (FIG. 9B), about 180 particles/mm² (FIG. 9D), and about 250 particles/mm² (FIG. 9F), respectively. The coated tubes were tested by ultrasound with a chicken breast as medium to record the images in. Of note, FIGS. 9A, 9C and 9E show a blank consisting of a chicken breast without tube; the FIGS. 9B, 9D, and 9F show the results with a chicken breast with a coated tube.

Figure 9:
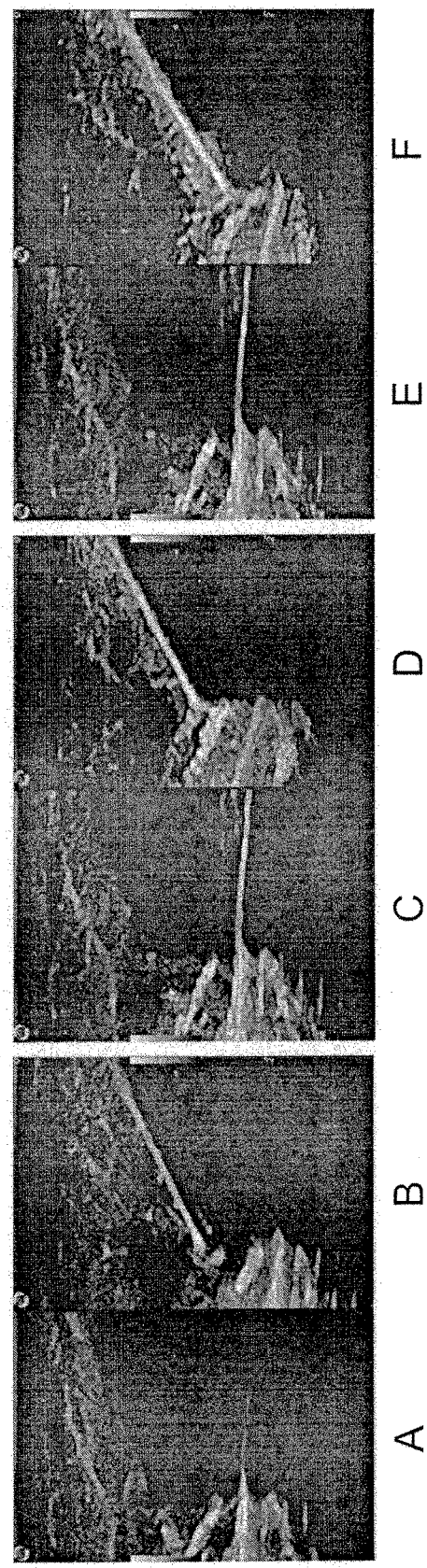
FIG. 9: Ultrasound images of coatings with about 130 (FIG. 9B), 180 (FIG. 9D) and 250 particles/mm$^2$ (FIG. 9F) and blanks (FIGS. 9A, 9C and 9E)

Studying the different tubes with ultrasound showed that for higher amounts of microparticles on the surface the surface of the tube starts to appear as rough, whereas at lower amounts the surface appears to be smooth (see FIG. 9). At lower amounts the visibility (sharpness of the image) improves.

Example 6

Solid glass microspheres with a diameter ranging from 38 to 45 µm, as described above in Example 1, were mixed through a polyurethane coating matrix. The microspheres were added in different amounts in order to prepare mixtures containing 1.0 to 75.0 vol. % microspheres in the coating matrix. Subsequently, either 30 or 60 µm thick marker bands of coating were drawn on glass slides using a film applicator. These marker bands were applied by masking the area which was required to be uncoated. The width of the marker bands was measured.

The coated substrates were measured by ultrasound using a 33 mm linear array probe operating in brightness-mode (B-mode) at 6 MHz. The substrates were placed under an approximate angle of 45 degrees inside a commercially available ultrasound phantom which acted as the medium.

Figure 10:
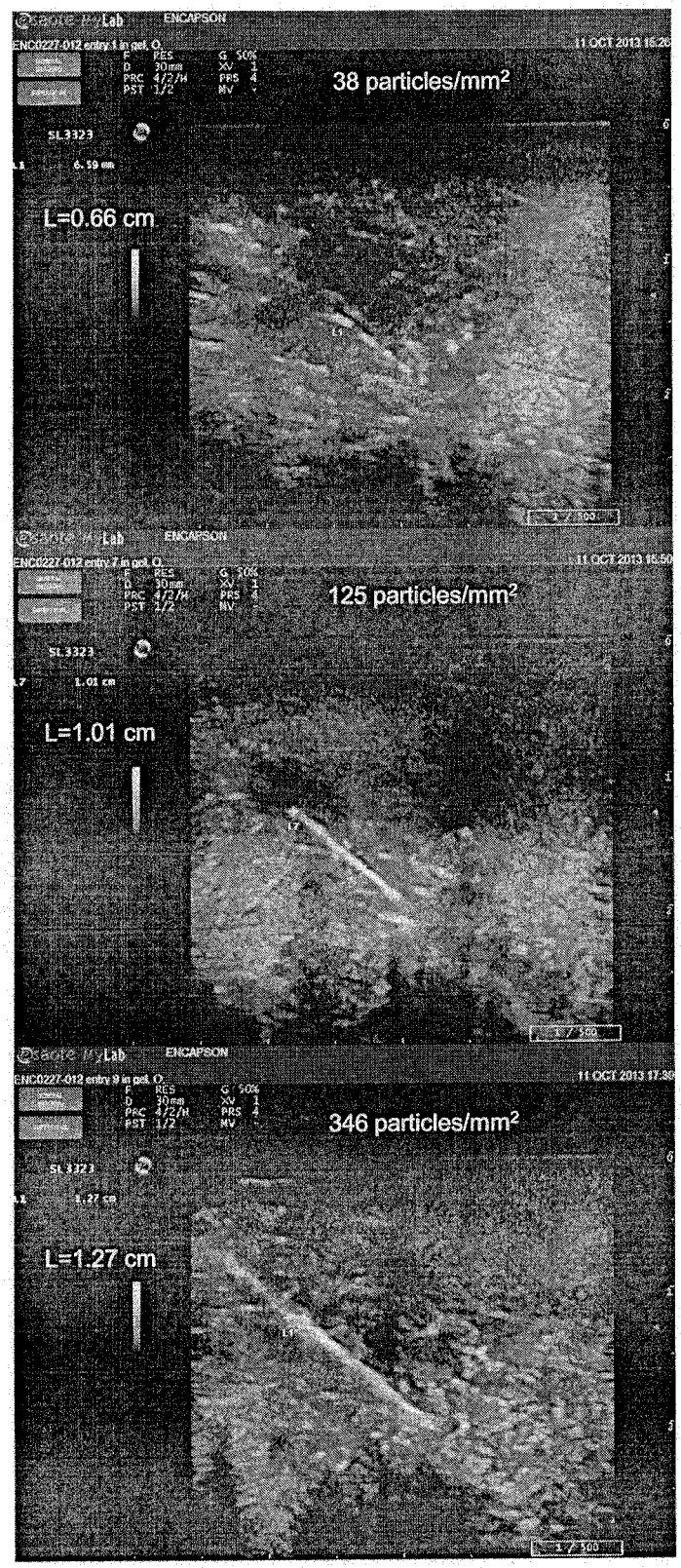
FIG. 10: Ultrasound images taken in a phantom gel of glass slides on which marker bands (width 1 cm) were applied of Sono-Coat coating comprising different concentrations of microspheres (size range 38-45 µm): about 38 (FIG. 10A), 125 (FIG. 10B) and 346 (FIG. 10C) particles/mm$^2$.

FIG. 10 shows ultrasound images taken in a phantom gel of glass slides on which marker bands (width 1 cm) were applied of Sono-Coat comprising the microspheres (size range 38-45 µm) in a concentration of 38 particles/mm² (FIG. 10A), 125 particles/mm² (FIG. 10B), and 346 particles/mm² (FIG. 10C). It is clear that FIG. 10B, which is within the density range of 45-150 particles/mm² according to the invention, provides the best visibility combined with an accurate measurement of the width of the marker band. FIG. 10C (density of 346 particles/mm²) is more vague and overestimation of the marker band width occurs, whereas the FIG. 10A is also more vague, appears as a dotted line and underestimates the width of the marker band.

Example 7

Figure 11:
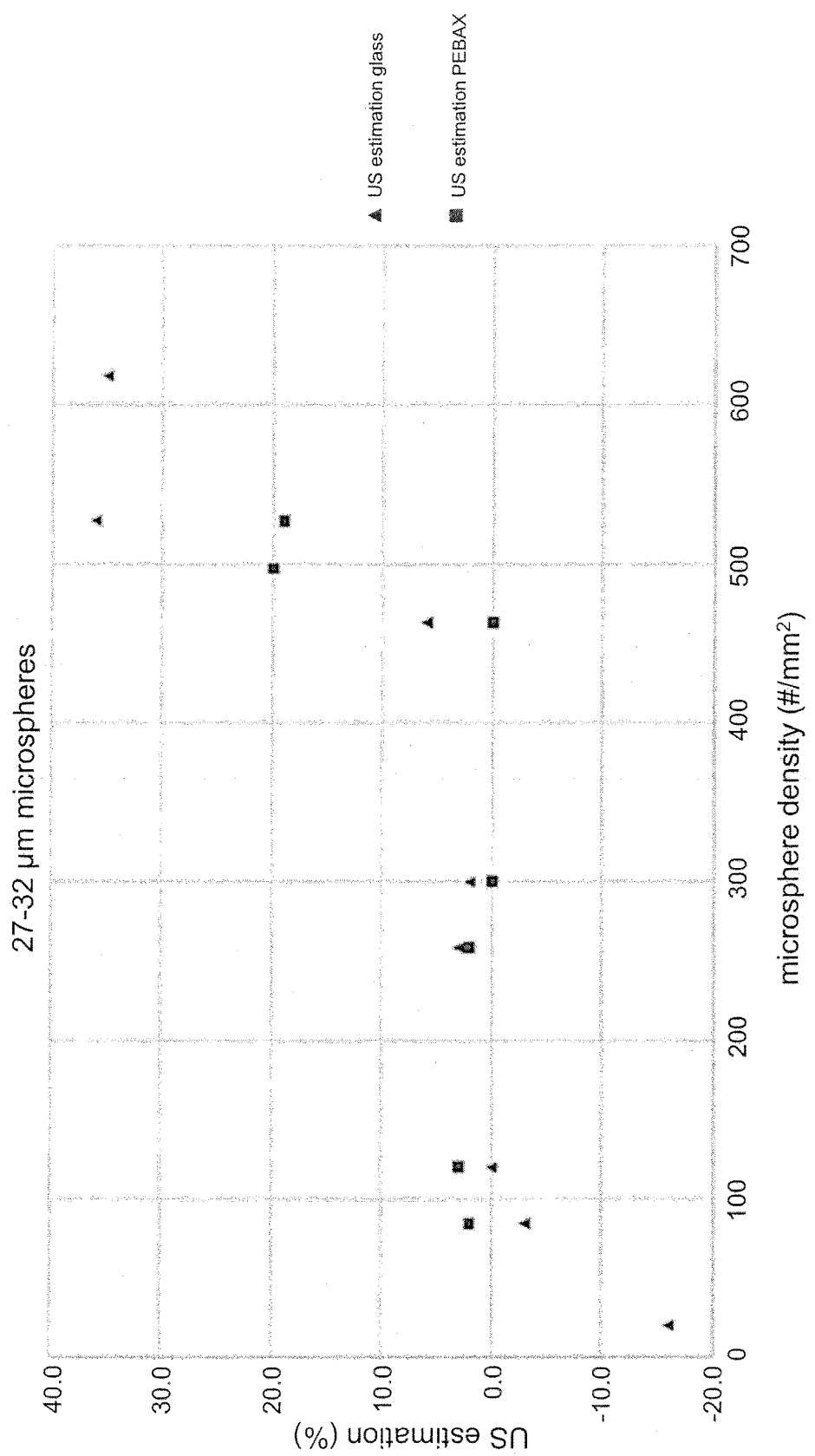
FIG. 11: US estimation error plotted against the microsphere density on glass and plastic surfaces coated with microspheres with a diameter between 27-32 µm.
Figure 12A:
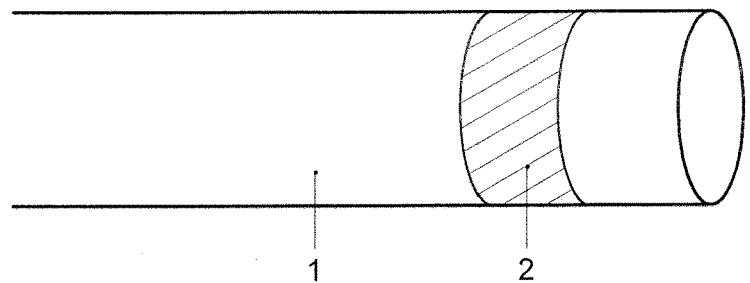
In FIG. 12A, device part 1 comprises a coating according to the invention applied as a marker band 12. Device part 1 can for example be a shaft of a catheter.
Figure 12B:
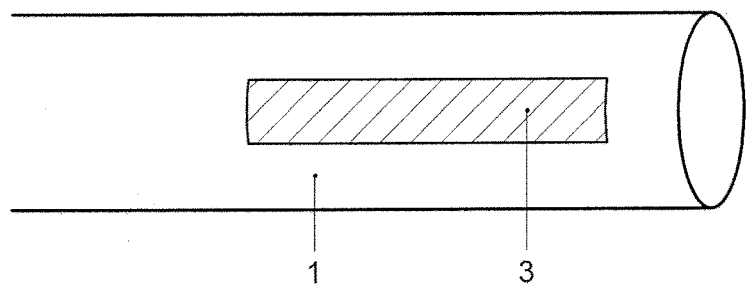
In FIG. 12B, the coating is applied as strip.
Figure 12C:
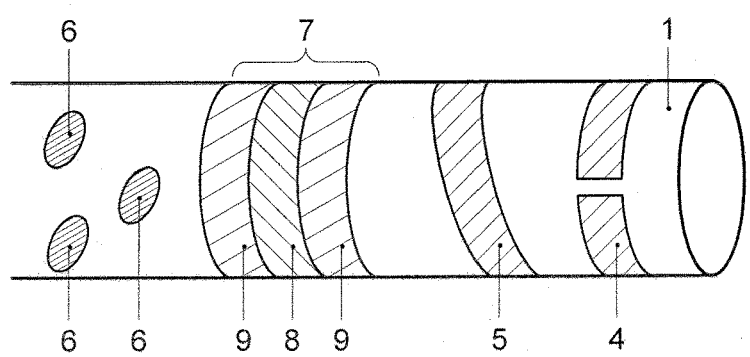
In FIG. 12C, various patterns for the coating are combined. The coating is applied in segments (4), in a spiral pattern (5), and as dots (6). Coating band 7 comprises a thinner band 8 with a high particle density alternating with thinner bands 9 with lower particle density. The contrast in the ultrasonic image provided with these coating patterns improves the visibility of the device.
Figure 12D:
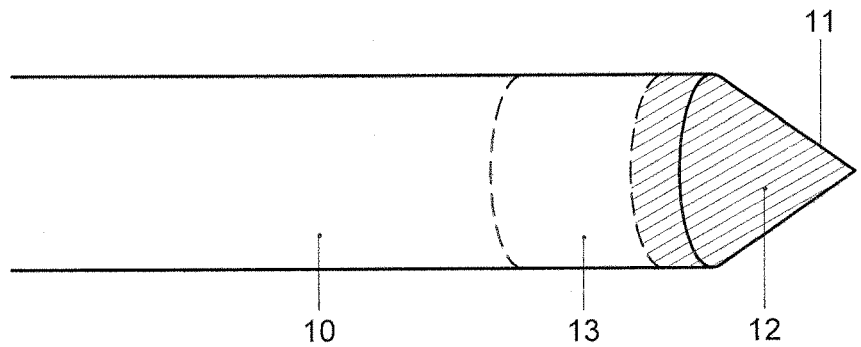
In FIG. 12D, device 10 comprises a tip part 11 coated with coating part 12 with a high surface density of the particles. Adjacent coating part 12 has a lower surface density of the particles.

The same kind of experiment as Example 2 was repeated. The same kind of 27-32 µm microspheres were used. These microspheres were coated on glass slides as well as on plastic (PEBAX polyether block amide) surfaces. In FIG. 11, the US estimation error is plotted against the microsphere density. From FIG. 11 it is clear that the optimum microsphere density range is the same for both the coated glass and the coated plastic surfaces. Like in FIG. 3, the optimum range for these microspheres is between 70 and 450 particles/mm². Hence, the visibility is dependent upon the scattering effect of the coating, not the surface itself.

Example 8

Commercially available solid glass microspheres (from Cospheric) with diameters ranging from 25 to 32 µm, with a density of 2.5 g/mL were mixed through a polyurethane coating matrix. Three different coating formulations were prepared containing 35% (w/w), 20% (w/w) and 10% (w/w) microspheres. From each coating formulation a 1 cm wide marker band was applied on a stainless steel type 304 needle (diameter 0.865 mm) by dip coating and masking the uncoated parts. Hence, three marker bands were obtained with a decreasing microsphere concentration, as arranged in the direction from the tip towards the shaft.

Figure 13:
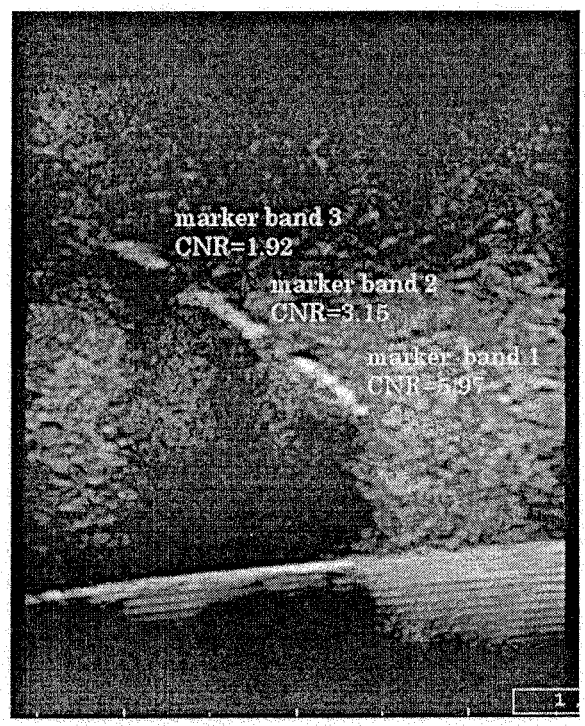
FIG. 13: Ultrasonography image of a needle comprising three marker bands with decreasing surface density of microspheres (size range 25-32 µm) in the direction of the needle tip alongside the shaft.

The coated needle was visualized by ultrasound using a 33 mm linear array probe operating in brightness-mode (B-mode) at 6 MHz. The needle was placed under an approximate angle of 45 degrees inside a commercially available ultrasound phantom which acted as the medium. An ultrasonogram of the needle containing three marker bands of different microsphere concentrations is depicted in FIG. 13. From FIG. 13 it is clear that the ultrasound visibility, expressed as the CNR, of the three marker bands decreased from the tip along the shaft (CNR 5.97, 3.15 and 1.92). FIG. 13 shows an ultrasonography image of a stainless steel type 304 needle (diameter 0.865 mm) comprising the three marker bands of Sono-Coat with decreasing surface density of microspheres (size range 25-32 µm) in the direction of the needle tip alongside the shaft. The ultrasound visibility, expressed as the CNR, decreases accordingly in the same direction. It has to be noted that the CNR values are not comparable to those obtained in the previous examples. The difference in CNR values is stemming from the difference in geometry of the substrates, i.e. a planar surface in comparison in the previous examples to a cylindrical surface this example.

Example 9

Figure 14:
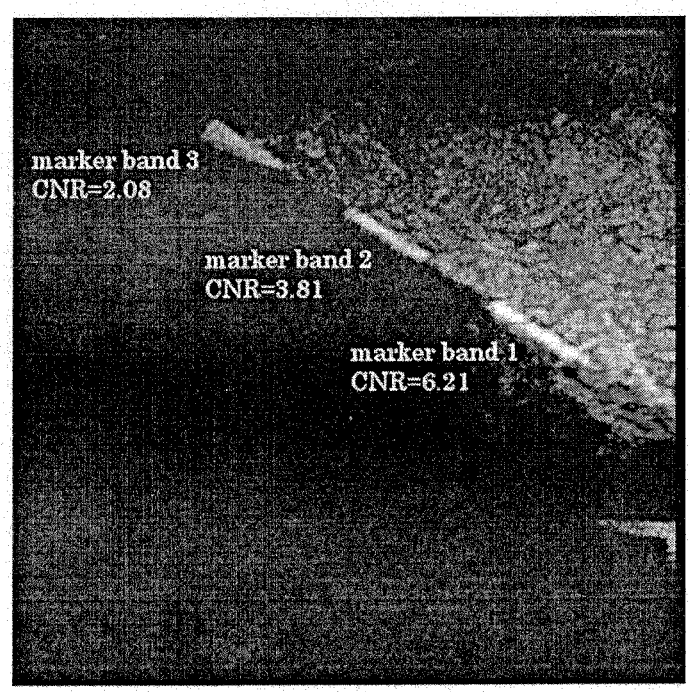
FIG. 14: Ultrasonography image of three marker bands applied onto a tube by spray coating.

Commercially available solid glass microspheres (from Cospheric) with diameters ranging from 25 to 32 µm, with a density of 2.5 g/mL were mixed through a polyurethane coating matrix. The concentration of microspheres in the coating matrix amounted to 47.5% (w/w). Three different marker bands were applied on a nylon 12 tube (diameter 6.0 mm) by spray coating and masking the uncoated parts. The microsphere surface density on the tube was varied by adjusting the spraying time, i.e. the spraying time for the marker band near the tip was 20 seconds, for the adjacent marker band 10 seconds and for the marker band located at the largest distance from the tip 5 seconds. The coated nylon 12 tube was visualized by ultrasound using a 33 mm linear array probe operating in brightness-mode (B-mode) at 6 MHz. The tube was placed inside a commercially available ultrasound phantom which acted as the medium. As can be seen in FIG. 14, the ultrasound visibility, expressed as the CNR, of the applied marker bands decreased with shortening of the spraying times (CNR 6.21, 3.81 and 2.08). FIG. 14 shows ultrasonography image of the three marker bands of Sono-Coat applied onto a nylon 12 tube (diameter 6.0 mm) by spray coating. The microparticle surface density was varied between the different marker bands by varying the spraying time, while maintaining the same spraying pressure and distance. The measured CNR values in this example are not comparable to those obtained in the previous examples due to a difference in geometry of the substrates.

Example 10

Figure 15:
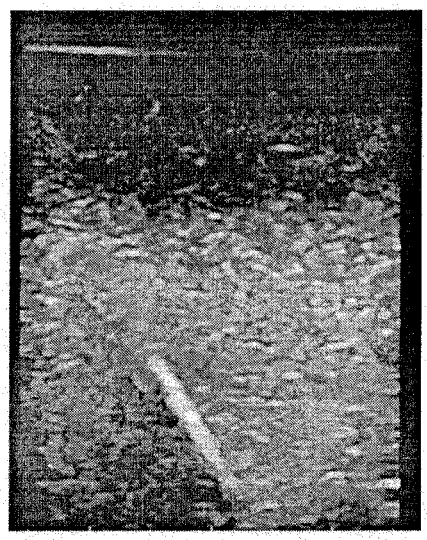
FIG. 15: Ultrasonography images of a device with an inventive coating and a device with a comparative coating.
Figure 15:
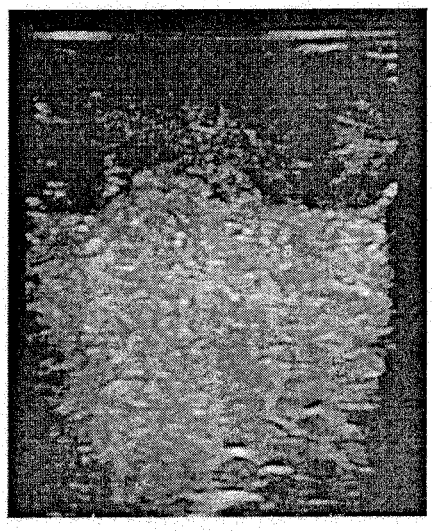
Figure 15:
Figure 15:
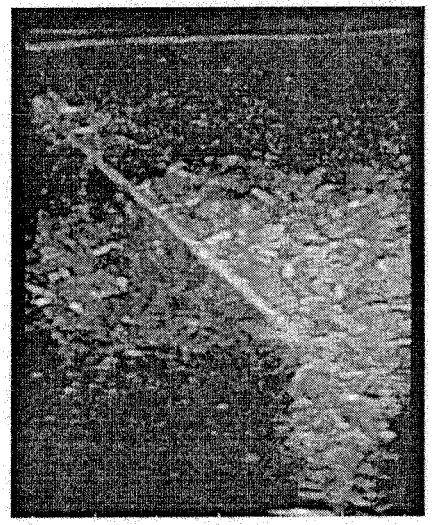

Device 1 is a needle completely coated with a comparative coating comprising glass particles with an average size of about 6.5 µm and a median size of about 6 µm. More than 60% by number of the particles are smaller than 10 um. The density is about 3400 particles per $mm^2$, as measured with optical microscopy. Device 2 is a wire provided with an inventive coating. The coating was applied as marker band over 2 cm length of the wire. The particle size was such that 60% of the particles had a particle size between 20 µm and 32 µm with an average diameter of 23 µm. The density was approximately 270 particles per $mm^2$ of the surface of the device. The results in FIG. 15 show ultrasonography images captured in a US gelatin phantom at an angle of about 60° (FIGS. 15A and 15B) and about 45° (figure C and D). Device 2 (FIGS. 15A and 15C) has much higher visibility than device 1 with a comparative coating (FIGS. 15B and 15D), even though the comparative coating has a higher density of particles. Device 2 in particular has better visibility at steeper angles.

REFERENCES

Baldelli et al (Eur. Radiol. 19 (2009); 2275-2285);
Couture et al., Ultrasound in Medicine and Biology, Vol. 32, No. 8, pp. 1247-1255, 2006;
Song et al (Applied Optics, Vol. 43, No. 5 (2004); 1053-1062);
EP 0624342; EP 1118337; U.S. Pat. Nos. 5,081,997; 5,289,831; 5,921,933;
U.S. Pat. No. 6,506,156; US 2004/0077948; US 2005/0074406; US 2009/0318746;
WO 98/18387; WO 00/51136; WO 00/66004; WO 2007/089761.

The invention claimed is:

1. A medical device comprising a coating for ultrasound detection, said coating comprising microparticles that are visible with ultrasound, wherein the microparticles are solid throughout, wherein the diameter of at least 60% of said microparticles on said medical device is between 10 and 45 µm and the density of said microparticles per surface area is between 45 and 450 particles/$mm^2$, and wherein said coating is applied as a pattern that spatially selectively covers parts of the surface.

2. The medical device according to claim 1, wherein said particles are essentially spherical.

3. The medical device according to claim 1, wherein said coating comprises one or more parts with a higher ultrasound visibility than adjacent coated or non-coated parts of the surface of the medical device.

4. The medical device according to claim 3, wherein said coating part has a contrast to noise (CNR) value that is at least 1.3 times higher than that of said adjacent parts of the surface of the medical device.

5. The medical device according to claim 1, wherein, in said parts,
the diameter of at least 60% of said microparticles on said medical device is between 22 and 45 µm and the density of said microparticles is between 45 and 450 particles/$mm^2$, or
the diameter of at least 60% of said microparticles on said medical device is between 22 and 27 µm and wherein the density of said microparticles on the surface of said medical device is between 150 and 450 particles/$mm^2$, or
the diameter of at least 60% of said microparticles on said medical device is between 27 and 32 µm and wherein the density of said microparticles on the surface of said medical device is between 70 and 450 particles/$mm^2$, or
the diameter of at least 60% of said microparticles on said medical device is between 32 and 38 µm and wherein the density of said microparticles on the surface of said medical device is between 45 and 225 particles/$mm^2$, or
the diameter of at least 60% of said microparticles on said medical device is between 38 and 45 µm and wherein the density of said microparticles on the surface of said medical device is between 45 and 150 particles/$mm^2$.

6. The medical device according to claim 1, wherein said microparticles comprise a material selected from the group consisting of polymers, ceramics, glasses, silicates, organic materials, metals and any combination thereof.

7. The medical device according to claim 1, wherein said coating comprises one or more strips with a width of 1 mm or more with a higher ultrasound visibility than adjacent coated or non-coated parts of the surface of the medical device.

8. The medical device according to claim 1, wherein the medical device has a tip, and wherein said coating comprises at least two marker bands alternating with uncoated parts of the surface of the medical device, and wherein adjacent marker bands have a different ultrasound visibility.

9. The medical device according to claim 1, wherein said coating comprises at least a first coated part and second coated part, wherein the average surface density of the microparticles in the first coated part differs from the average surface density of the microparticles in the second coated part.

10. The medical device according to claim 1, wherein said coating comprises at least a first part and second part, each of said parts having a surface of at least 0.010 $mm^2$, the parts being adjacent to each other or separated by a separator, said separator selected from the group consisting of:
an uncoated part of the surface of the medical device, a coating part being essentially free of said microparticles, and a coating part having a contrast-to-noise ratio lower than 1.5, the first part and the second part being different in at least one of:

the second part having a surface density of said microparticles at least 0.1 times the surface density of said microparticles of the first part, the microparticles of the first part having a number average particle size at least 1.2 times higher than the microparticles of the second part, and the second part having a surface density of particles with a diameter between 10 and 45 µm, that is at least 0.1 times higher than the surface density of such particles in the first part, wherein the surface density is expressed in number of particles per $mm^2$ surface of said medical device.

11. The medical device according to claim 1, wherein in a first coated part and a second coated part one or more of conditions A), B), C), D), and E) applies, provided that the condition for the first coated part is different from the condition for the second coated part, wherein the conditions are selected from the group consisting of:

A) the diameter of at least 60% of said microparticles on said medical device is between 22 and 45 µm and wherein the density of said microparticles on the surface of said medical device is between 45 and 450 particles/$mm^2$, B) the diameter of at least 60% of said microparticles on said medical device is between 22 and 27 µm and wherein the density of said microparticles on the surface of said medical device is between 150 and 450 particles/$mm^2$, C) the diameter of at least 60% of said microparticles on said medical device is between 27 and 32 µm and wherein the density of said microparticles on the surface of said medical device is between 70 and 450 particles/$mm^2$, D) the diameter of at least 60% of said microparticles on said medical device is between 32 and 38 µm and wherein the density of said microparticles on the surface of said medical device is between 50 and 275 particles/$mm^2$, and E) the diameter of at least 60% of said microparticles on said medical device is between 38 and 45 µm and wherein the density of said microparticles on the surface of said medical device is between 10 and 250 particles/$mm^2$.

12. The medical device according to claim 10, wherein said first and second part are each a marker band on a curved surface of a shaft of said medical device, separated from each other in the axial direction of said shaft by said separator.

13. The medical device according to claim 10, wherein the first part has a surface density of particles with a diameter between 10 and 45 µm, that is at least 1.2 times higher than the surface density of such particles in the second part, the surface density in number particles per $mm^2$ surface of said medical device.

14. The medical device according to claim 1, wherein said particles are essentially spherical.

15. A method for preparing a medical device according to claim 1, the method comprising:

providing a medical device, and coating said medical device with a coating comprising microparticles that are visible with ultrasound in a non-uniform way, such that the diameter of at least 60% of said microparticles on said medical device is between 10 and 45 µm and the density of said microparticles on the surface of said medical device is between 45 and 450 particles/$mm^2$.

16. The method according to claim 15, wherein said medical device is coated with said coating that comprises said microparticles that are visible with ultrasound, such that the diameter of at least 60% of said microparticles on said medical device is between 22 and 45 µm and the density of said microparticles on the surface of said medical device is between 45 and 450 particles/$mm^2$.

* * * * *